United States Patent [19]

Farina et al.

[11] Patent Number: 5,162,521

[45] Date of Patent: Nov. 10, 1992

[54] PROCESSES FOR MAKING CEPHEMS FROM ALLENYLAZETIDINONE DERIVATIVES

[75] Inventors: Vittorio Farina, West Hartford, Conn.; Stephen R. Baker, Cicero, N.Y.

[73] Assignee: Bristol-Myers Squibb Company, New York, N.Y.

[21] Appl. No.: 711,250

[22] Filed: Jun. 6, 1991

[51] Int. Cl.$^5$ .......................................... C07D 501/02
[52] U.S. Cl. ................................. 540/226; 540/227; 540/221
[58] Field of Search ............... 540/222, 221, 226, 227

[56] References Cited

U.S. PATENT DOCUMENTS

| | | | |
|---|---|---|---|
| 4,066,641 | 1/1978 | Hamashima et al. | 544/17 |
| 4,147,864 | 4/1979 | Woodward et al. | 544/16 |
| 4,267,340 | 5/1981 | Kamiya et al. | 548/187 |
| 4,550,162 | 10/1985 | Woodward et al. | 544/16 |
| 4,798,890 | 1/1989 | Torii et al. | 540/358 |

OTHER PUBLICATIONS

Farina et al., *Tetrahedron Letters*, "Palladium Catalysis in Cephalosporin Chemistry", 29, No. 47, p. 6043 (1988).

Conway et al., *Canadian Journal of Chemistry*, "Nuclear Analogs of β-Lactam Antibiotics", 56, p. 1335 (1978).

Hamashima et al., *Heterocycles*, "Synthesis of 3-Substituted Cephems from Penicillins via 4-Dithio-2-Azetidinone Intermediates", 5, p. 419 (1976).

Scartazzini et al., *Helvetica Chimica Acta*, "Neue β-Lactam-Antibiotika", 58, p. 2437 (1975).

Farina et al., *Journal of Organic Chemistry*, "A General Route to- 3-Functionalized 3-Norcephalosporins", 54, p. 4962 (1989).

Kant et al., *Tetrahedron Letters*, "Reactions of Organocuprates with Vinyl Triflates and Related Cephems", 31, No. 24, p. 3389 (1990).

*Primary Examiner*—Nicholas S. Rizzo
*Attorney, Agent, or Firm*—William T. Han

[57] ABSTRACT

This invention relates to a novel process for making a cephem of formula II from 2-(3-amino-2-oxo-azetidin-1-yl)-2,3-butadienoate of formula I. In another aspect, this invention is concerned with a process of further converting a compound of formula II into an antibacterial cephem of formula III.

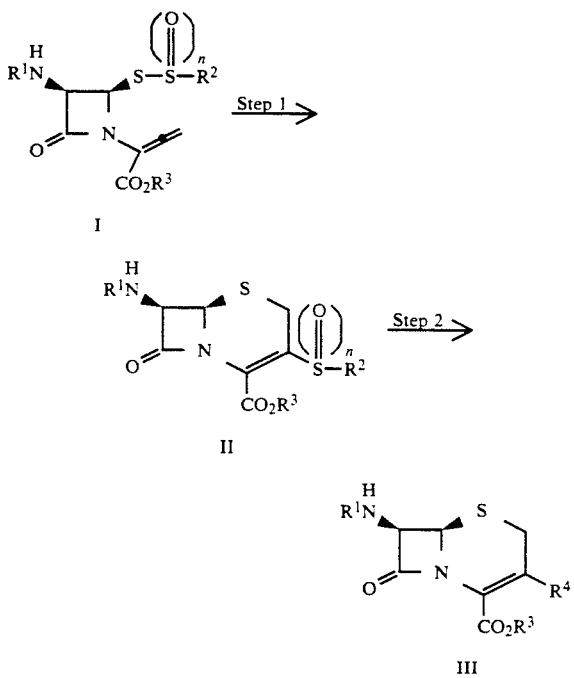

In formulae I, II and III, $R^1$ is hydrogen, a conventional amino protecting group or an acyl group; $R^2$ is an aromatic heterocyclic or aryl group; $R^3$ is a conventional carboxy protecting group or $-CO_2R^3$ taken together forms a physiologically hydrolyzable ester; and $R^4$ is a group selected from the group consisting of $C_{1-6}$ alkyl, $C_{2-6}$ alkenyl, $C_{2-6}$ alkynyl, cyclic $C_{3-6}$ alkyl, and aryl; and n is 0 or 2.

17 Claims, No Drawings

PROCESSES FOR MAKING CEPHEMS FROM ALLENYLAZETIDINONE DERIVATIVES

BACKGROUND OF THE INVENTION

1. Field of Invention

This invention relates to a novel process for making antibacterial cephalosporins from allenylazetidinone derivatives.

More specifically, as shown in Scheme (A), the process involves converting 2-(3-amino-2-oxo-azetidin-1-yl)-2,3-butadienoate of formula I into C-3 aromatic heterocyclicthio, arylthio, aromatic heterocyclicsulfonyl, or arylsulfonyl cephalosporins of formula II and further replacing said C-3 group with a group such as cis-propenyl found in cefprozil, a broad spectrum antibiotic.

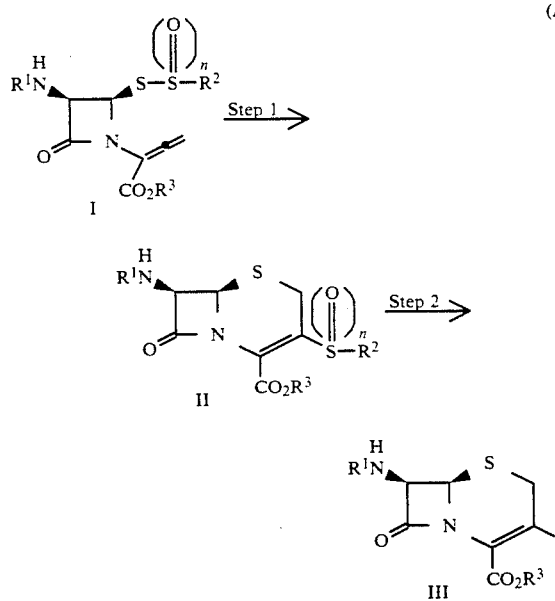

In Scheme (A), $R^1$, $R^2$, $R^3$, $R^4$, and n are defined hereinbelow. Preferable reagents used in step 1 and step 2 are lithium halide and an organo-stannane, $n$-$Bu_3SnR^4$, along with a palladium (0) catalyst, respectively.

2. Description of Related Art

Farina et al., in Tetrahedron Letters, 29, No. 47, p. 6043 (1988), disclose reactions of C-3 trifloxy cephalosporins of formula IV with organo-stannanes in the presence of a palladium (0) catalyst to transfer a variety of $R^6$ radicals. Examples of $R^6$ radicals include alkenyl, alkynyl and aryl.

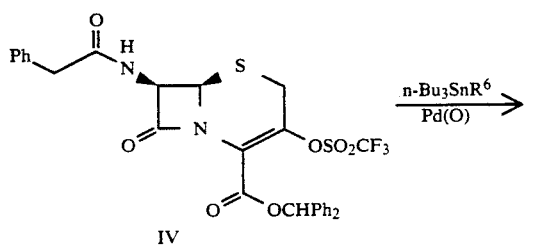

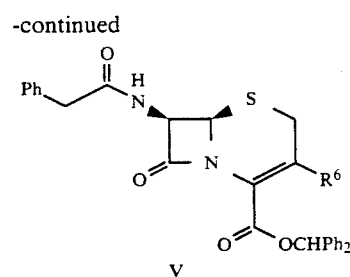

The instant process of displacing the C-3 aromatic heterocylicthio, arylthio, aromatic heterocyclicsulfonyl or arylsulfonyl group with a $R^4$ group using an organo-stannane reagent and a palladium (0) catatylst has never been reported.

Conway et al., in the *Canadian Journal of Chemistry*, 56, p 1335 (1978), disclose the allene derivative of formula VI.

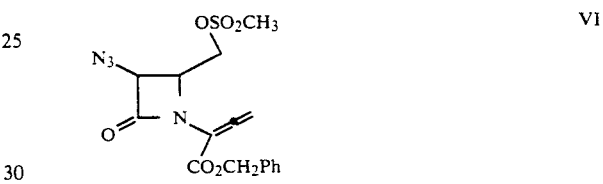

Due to the direct attachment of a methylene group to the C-4 position of the azetidinone ring, the compound of formula VI cannot be directly converted to a cephem structure.

U.S. Pat. No. 4,066,641, issued to Hamashima et al. on Jan. 3, 1978, discloses a process of cephem preparation, as depicted in Scheme (C), by a base induced ring closure of compound of formula VII.

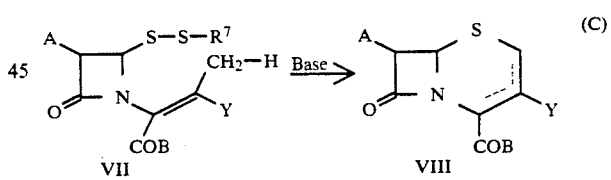

wherein

A is amino or substituted amino;

COB is carboxy or protected carboxy;

$R^7$-S can be substituted thio such as benzothiazol-2-ylthio, thiazol-2-ylthio and acetylthio;

Y is an electron drawing group from acyloxy, halogen, cyano, nitro and nitroso; and the dotted line shows $\Delta^2$ or $\Delta^3$ double bond.

The present invention provides methods for the exclusive formation of the $\Delta^3$ cephem isomers.

Similar to the process depicted in Scheme (C) above, U.S. Pat. No. 4,147,864, issued to Woodward et al. on Apr. 3, 1979, relates to a base promoted cyclization of the compounds of formula IX into the cephems of formula X

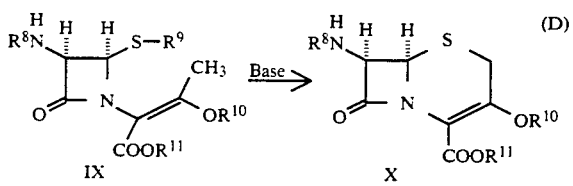

wherein $R^8$ is an acyl group; $R^9$ represents an optionally substituted aromatic heterocyclic radical with up to 15, preferably up to 9, carbon atoms and at least one ring nitrogen atom and optionally a further ring heteroatom, such as oxygen or sulfur, which radical is bonded to the thio group —S— by one of its ring carbon atoms, which is bonded to a ring nitrogen atom by a double bond, or $R^9$ is —$SO_2Q'$ in which $Q'$ is an optionally substituted aliphatic, cycloaliphatic, araliphatic or aromatic hydrocarbon with up to 18, preferably up to 10, carbon atoms; $R^{10}$ includes a group such as lower alkyl; and $R^{11}$ represents hydrogen or a carboxy protecting group.

U.S. Pat. No. 4,550,162 issued to Woodward et al., on Oct. 29, 1985, discloses compounds similar to cephalosporins of formula IX above in which $R^8$, $R^9$ and $R^{11}$ have the same meaning as above, but $R^{10}$ has the meaning of —$SO_2Q'$ as defined above.

U.S. Pat. 4,267,340, issued on May 12, 1981 to Kamiya et al., discloses, inter alia, the azetidinone derivatives of the formula XI. As shown in Scheme (E), the azetidinones of formula XI can be converted into the cephams of formula XII with an electrophilic reagent $X_2$ such as chlorine.

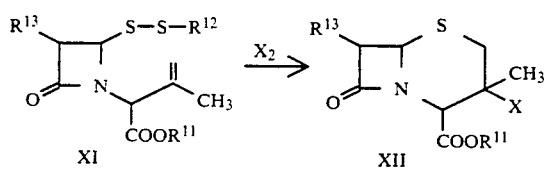

In Scheme (E), $R^{13}$ represents a substituted or unsubstituted amino radical; $R^{12}$ is a substituted or unsubstituted heterocyclic group such as oxazolyl, benzoxazolyl, thiazolyl, benzothiazolyl, benzimidazolinyl and imidazolinyl; $R^{11}$ is hydrogen or a carboxy protecting group.

U.S. Pat. No. 4,798,890, issued to Torii et al. on Jan. 17, 1989, relates to the formation of the compounds of formula XIV, which are reported to be useful precursors to cephems, from the compounds of formula XIII.

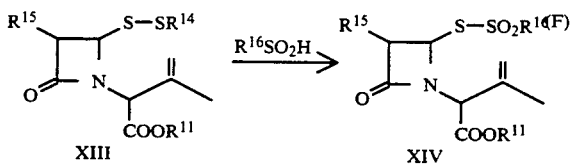

In formulae XIII and XIV, $R^{15}$ can represent amino or acylamino, $R^{14}$ is a substituted or unsubstituted nitrogen-containing aromatic heterocyclic residue, $R^{11}$ is hydrogen or a carboxy protecting group, and $R^{16}$ is substituted or unsubstituted phenyl.

A number of C-3 aromatic heterocyclicthio cephems are already known. For example Hamashima et al., in Heterocycles, 5, p. 419 (1976), and Scartazzini et al., in [Helvetica Chimica Acta, 58, p 2437 (1975) disclose the cephems of formulae XV and XVI, respectively.

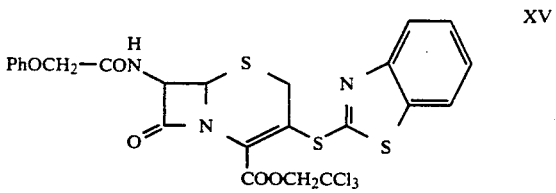

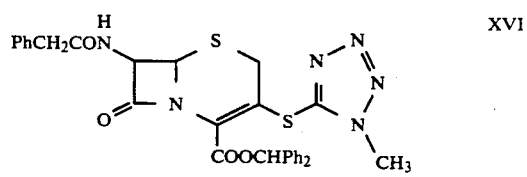

Typically, C-3 aromatic heterocyclicthio cephems such as shown as structures XV and XVI have been made by the displacement of a C-3 leaving group with an aromatic heterocyclic mercaptan. For example, Farina et al., in the Journal of Organic Chemistry, 54, p. 4962 (1989), disclose triflate (trifluorosulfonyloxy) as such C-3 leaving group. To Applicants knowledge, none of the syntheses of the C-3 aromatic heterocyclicthio cephems reported to date has involved direct cyclization of 2-(2-oxo-azetidin-1-yl)-2,3-butadienoates [allenylazetidinones] of formula I of the present application.

Kant et al., in Tetrahedron Letters. 31, No. 24, p. 3389 (1990), disclose the reaction of the compound of formula XVI with lithium dimethylmethyl cuprate to afford the compound of formula V'.

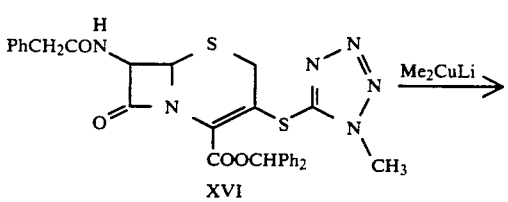

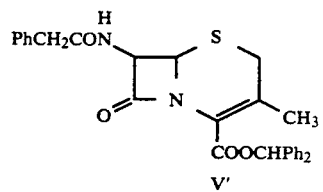

However, the art does not teach that organo-stannanes can be used in lieu of the cuprates to displace C-3 aromatic heterocylicthio groups in cephalosporins.

SUMMARY OF THE INVENTION

As shown in Scheme (A), this invention relates to a novel process for making a cephem of formula II from 2-(3-amino-2-oxo-azetidin-I-yl)-2,3-butadienoate of formula I. In another aspect, this invention is concerned with a process of further converting a compound of formula II into an antibacterial cephem of formula III.

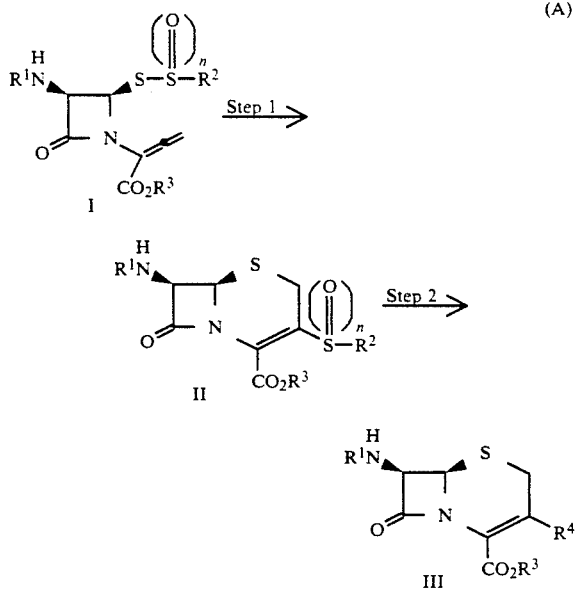

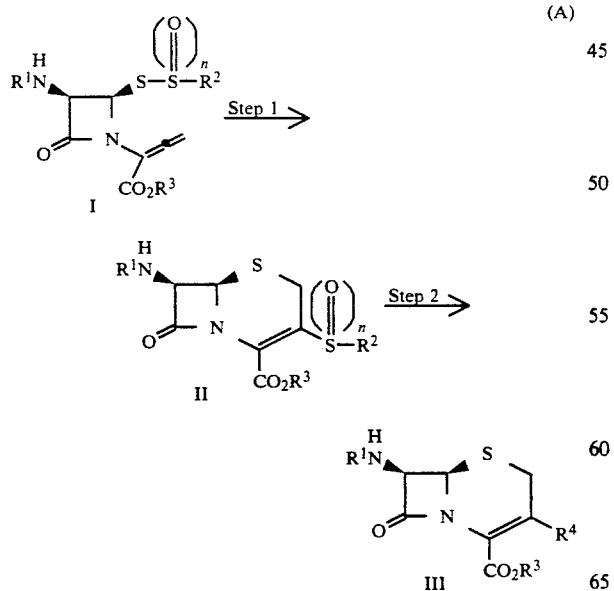

In the compounds of Scheme (A), $R^1$ is hydrogen, a conventional amino protecting group or an acyl group; $R^2$ is an aromatic heterocyclic or aryl group; $R^3$ is a conventional carboxy protecting group or —$CO_2R^3$ taken together forms a physiologically hydrolyzable ester; and $R^4$ is a group selected from the group consisting of $C_{1-6}$ alkyl, $C_{2-6}$ alkenyl, $C_{2-6}$ alkynyl, cyclic $C_{3-6}$ alkyl, and aryl; and n is 0 or 2.

DETAILED DESCRIPTION OF THE INVENTION

This invention relates to a novel process, as shown in Scheme (A), for making a cephem of formula II from 2-(3-amino-2-oxo-azetidin-1-yl)-2,3-butadienoate of formula I. In another aspect, this invention is concerned with a process of further converting a compound of formula II into an antibacterial cephem of formula III.

In the compounds of Scheme (A), $R^1$ is hydrogen, a conventional amino protecting group or an acyl group; $R^2$ is an aromatic heterocyclic or aryl group; $R^3$ is a conventional carboxy protecting group or —$CO_2R^3$ taken together forms a physiologically hydrolyzable ester; and $R^4$ is a group selected from the group consisting of $C_{1-6}$ alkyl, $C_{2-6}$ alkenyl, $C_{2-6}$ alkynyl, cyclic $C_{3-6}$ alkyl, and aryl; and n is 0 or 2.

More specifically, in compounds of Scheme (A), when $R^1$ is an acyl group as distinguished from a conventional amino protecting group, said acyl group is selected from the pharmacologically active C-7 or C-6 acyl side chains found in the respective cephalosporin or penicillin antibiotic art. Preferable acyl group is that from the cephalosporin art. A recent review by Durckheimer et al., "Recent Developments in the Field of Cephem Antibiotics", *Advances in Drug Research*, 17, pp 61–234 (1988), offers a comprehensive overview of cephalosporin antibiotic art and possible C-7 acyl side chains.

When the acyl group $R^1$ is represented by a radical $R^aCO—$, preferred $R^a$ is hydrogen;

$C_{1-6}$ alkyl, $C_{1-6}$ alkyl substituted by cyano, carboxy, halogen, amino, $C_{1-6}$ alkyloxy, $C_{1-6}$ alkylthio, trifluoromethyl, or trifluoromethylthio;

a phenyl or substituted phenyl group represented by the formula

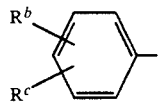

wherein $R^b$ and $R^c$ independently are hydrogen, halogen, hydroxy, $C_{1-6}$ alkyloxy, $C_{1-6}$ alkyl, $C_{1-6}$ alkylthio, amino, mono- or di($C_{1-6}$ alkyl)amino, $C_{1-6}$ alkanoylamino, $C_{1-6}$ alkylsulfonylamino, carboxy, carbamoyl, hydroxymethyl, aminomethyl, or carboxymethyl;

a group presented by the formula

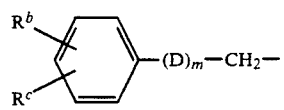

wherein $R^b$ and $R^c$ have the same meanings as defined above, D is oxygen or sulfur, and m is 0 or 1;

a heteroarylmethyl group represented by the formula

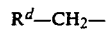

wherein $R^d$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_{1-6}$ alkyl, $C_{1-6}$ alkyloxy, $C_{1-6}$ alkysulfonylamino;

a substituted methyl group represented by the formula

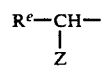

wherein $R^e$ is oyclohexa-1,4-dienyl, or a phenyl group or substituted phenyl group

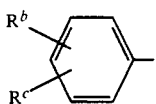

wherein $R^b$ and $R^c$ have the above defined meanings, or $R^e$ is $R^d$ as defined above, and Z is hydroxy, $C_{1-6}$ alkanoyloxy, carboxy, sulfo, or amino;
a keto group or an oximino-substituted group represented by the formulae

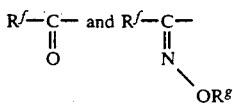

wherein $R^f$ is $R^d$ or $R^e$ as defined above and $R^g$ is hydrogen, $C_{1-6}$ alkyl, cyclic $C_{3-6}$ alkyl or a radical selected from the formulae

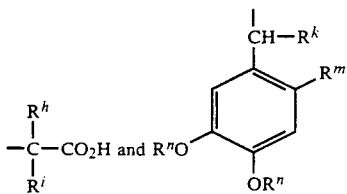

in which $R^h$ and $R^i$ are independently hydrogen, methyl or ethyl, or $R^h$ and $R^i$, taken together with the carbon atom to which they are attached, may be a cycloalkylidene ring containing from 3 to 5 carbon atoms, $R^k$ and $R^m$ are hydrogen or carboxy, with the proviso that both cannot be the same, and $R^n$ is hydrogen or acetyl; or
an alkylidene group of the formulae

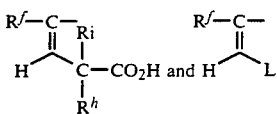

in which L is halogen or $CF_3$, and $R^f$, $R^i$ and $R^h$ are as defined above.

More preferred $R^a$ group is a radical selected from the group

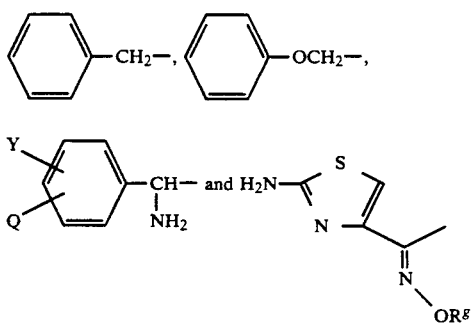

in which Y and Q are independently hydrogen, hydroxy or halogen; $R^g$ is hydrogen, $C_{1-6}$ alkyl, cyclic $C_{3-6}$ alkyl or a radical of the formula

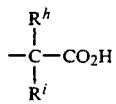

in which $R^h$ and $R^i$ are as defined above.

In the instant application, the numbers in subscript after the symbol "C" define the number of carbon atoms a particular group could contain. For example, in the above definition of the compounds in Scheme (A), $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl and the like alkyl groups. Similarily, $C_{1-6}$ alkyloxy (alkoxy) refers straight or branched alkyloxy groups such as methoxy, ethoxy, n-propoxy, i-propoxy, n-butoxy, t-butoxy, n-pentyloxy, n-hexyloxy, 3-methylpentyloxy, to name a few; $C_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl and the like groups; $C_{2-6}$ alkynyl refers to straight or branched chain alkynyl groups such as ethynyl, 1-propynyl, propargyl, 1-hexynyl, 2-hexynyl and the like groups; $C_{1-6}$ akanoyloxy refers to groups such as formyloxy, acetoxy (acetyloxy), propanoyloxy, 3-methylpentanoyloxy and the like groups; cyclic $C_{3-6}$ alkyl refers to groups such as cyclopropyl, cyclobutyl, cyclopentyl, cyclohexyl, cyclopropylmethyl, cyclopropylethyl, cyclopropylpropyl, cylcobutylmethyl, cyclobutylethyl, cyclopentylmethyl and the like groups; aryl group refers to unsubstituted phenyl or phenyl independently substituted with one to three halogen, $C_{1-6}$ alkyl, $C_{1-6}$ alkyloxy or $C_{1-6}$ alkylthio such as 4-methylphenyl, 2,3-dimethoxyphenyl, 2-methyl-3-ethoxylphenyl, 4-t-butoxyphenyl, 4-methylthio-3-fluorophenyl, 2,4-dichlorophenyl, 2-chloro-4-bromophenyl and the like groups; di($C_{1-6}$ alkyl)amino refers to disubstituted amino groups in which the two substituents may be the same or different, such as dimethylamino, N-ethyl-N-methylamino, N-ethyl-N-propylamino, diethylamino and the like groups; $C_{1-6}$ alkyl substituted by cyano refers to cyanomethyl, cyanoethyl, 4-cyanobutyl and the like; $C_{1-6}$ alkyl substituted by carboxy refers to such groups as carboxymethyl, 2-carboxyethyl, 2-carboxypropyl, 4-carboxybutyl, 5-carboxypentyl and the like; halogen refers to fluorine, chlorine, bromine, or iodine; thus, $C_{1-6}$ alkyl substituted by halogen refers to chloromethyl, bromomethyl, 2-chloroethyl, 1-bromoethyl, 4-chlorobutyl, 4-bromopentyl, 6chlorohexyl, 4-fluorobutyl, 3-fluoropropyl, fluoromethyl and the like; $C_{1-6}$ alkyl substituted by amino refers to such groups as 2-aminoethyl, aminomethyl, 3-aminopropyl, and 4-aminobutyl and the like groups; $C_{1-6}$ alkyl substituted by $C_{1-6}$ alkyloxy (alkoxy) refers to methoxymethyl, 2-methoxyethyl, 2-ethoxyethyl, ethoxymethyl, 3-propoxypropyl, 3-ethoxybutyl, 4-t-butoxybutyl, 3-methoxypentyl, 6-methoxyhexyl, 5-pentyloxyhexyl and the like groups; $C_{1-6}$ alkyl substituted by $C_{1-6}$ alkythio refers to such groups as methylthiomethyl, 2-methylthioethyl, 2-ethylthiopropyl, 4-methylthiobutyl, 5-ethylthiohexyl, 3-t-butylthiopropyl, 3-hexylthiopropyl and the like groups; $C_{1-6}$ alkyl substituted by trifluoromethyl is exemplified by 2,2,2-trifluoroethyl, 3,3,3-trifluoropropyl, 4,4,4-trifluorobutyl and the like; and $C_{1-6}$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl and the like $C_{1-6}$ alkyl substituted groups.

When $R^a$ is a substituted phenyl group wherein the substituents are represented by $R^b$ and $R^c$, examples of such groups are halophenyl such as 4-chlorophenyl, 3-bromophenyl, 2-fluorophenyl, 2,4-dichlorophenyl and 3,5-dichlorophenyl; hydroxyphenyl such as 2-hydroxyphenyl, 3-hydroxyphenyl, 4-hydroxyphenyl, 2,4-dihydroxyphenyl and 3,4-dihydroxyphenyl; alkyloxyphenyl such as 2,6-dimethoxyphenyl, 4-methoxyphenyl, 3-ethoxyphenyl, 3,4-dimethoxyphenyl, 4-t-butoxyphenyl, 4-methoxy-3-ethoxyphenyl and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl and 3,5-dimethylphenyl; alkylthiophenyl such as 4-methylthiophenyl, 3-n-butylthiophenyl, 2-ethylthiophenyl, 3,4-dimethylthiophenyl and 3-n-propylthiophenyl; aminophenyl such as 2-aminophenyl, 4-aminophenyl, 3,5-diaminophenyl and 3-aminophenyl; alkanoylaminophenyl such as 2-acetylaminophenyl, 4-acetylaminophenyl, 3-propionylaminophenyl and 4-butyrylaminophenyl; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl and 3-ethylsulfonylaminophenyl; carboxyphenyl such as 2-,3-, or 4-carboxyphenyl, 3,4-dicarboxyphenyl and 2,4-dicarboxyphenyl; carbamoylphenyl such as 2-carbamoylphenyl, 2,4-dicarbamoylphenyl and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butoxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-methoxy-3-hydroxyphenyl, 4-methylsulfonylamino-2-carboxyphenyl, 4-amino-3-chlorophenyl and 2-carboxymethyl-4-hydroxyphenyl.

Examples of $R^aCO$-groups wherein $R^a$ is a group represented by the formula

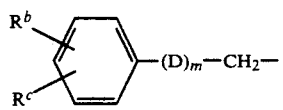

with m equals 0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl and 4-acetylaminophenylacetyl; and with m equals 1 and D equals oxygen, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m equals 1 and D equals sulfur, phenylthioacetyl, 4-chlorophenylthioacetyl, 3,4-dichlorophenylthioacetyl, 2-fluorophenylthioacetyl, 3-hydroxyphenylthioacetyl and 4-ethoxyphenylthioacetyl.

Examples of $R^d$-$CH_2CO$ groups wherein $R^d$ is a heteroaryl group are 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl and the like heteroaryl groups optionally substituted by amino, $C_{1-6}$ alkylsulfonylamino, hydroxy, halogen, $C_{1-6}$ alkyl or $C_{1-6}$ alkyloxy groups.

Examples of $R^aCO$-groups wherein $R^a$ is a substituted methyl group represented by the formula $R^e$—CH(Z)— and Z is amino, carboxy, hydroxy, $C_{1-6}$ alkanoyloxy, or sulfo are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohexa-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2yl)acetyl.

Examples of $R^aCO$ acyl groups in which $R^a$ is a keto group or an oximino-substituted group represented by the formulae

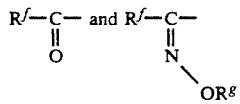

are the keto groups such as 2-oxo-2-phenylacetyl, 2-oxo-2-(2-thienyl)acetyl and 2-oxo-2-(2-aminothiazol-4-yl)acetyl; and the oximino-substituted groups such as 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(5-amino-1,2,4-thiadiazol-3-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoyl-prop-2-yl)oxyiminoacetyl and 2-(5-amino-1,3,4-thiadiazol-2-yl)-2-methoxyiminoacetyl.

Examples of $R^aCO$ acyl groups wherein $R^a$ is an alkylidene represented by the formulae

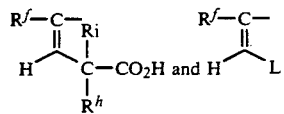

are 2-(2-aminothiazol-4-yl)-2-(2,2-dimethyl-2-carboxyethylidene)acetyl, 2-(2-aminothiazol-4-yl)-2-(2-trifluoroethylidene)acetyl and the like.

As used in the instant invention, an aromatic heterocylic group $R^2$, as opposed to a heteroaryl group $R^d$ defined previously, refers to a five-membered aromatic heterocyclic ring containing 1 to 4 nitrogen atoms, and up to 1 sulfur or 1 oxygen atom, said five-membered ring optionally substituted with up to four $C_{1-6}$ alkyl groups or a benzo group; or said aromatic heterocylic group also refers to a six-membered aromatic heterocylic ring containing 1 to 4 nitrogen atoms and optionally substituted with up to four $C_{1-6}$ alkyl groups. Said aromatic heterocylic group is connected to the C-3 sulfur atom of the cephalosporins through an unsubstituted carbon atom in the ring. Preferred aromatic heterocylic groups include groups such as benzothiazol-2-yl, benzooxazol-2-yl, 1-methylbenzimidazol-2-yl, 2-pyridyl, oxazol-2-yl, thiazol-2-yl, 1-methyl-1,2,3,4-tetrazol-5-yl and 1-methylimidazol-2-yl.

Conventional carboxy-protecting groups which can be employed in the present invention to block or protect the carboxylic acid function are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxy-protecting groups include moieties such as $C_{1-6}$ alkyl, diphenylmethyl (benzyhydryl), 2-naphthylmethyl, 4-pyridylmethyl, phenacyl, acetonyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl $C_{1-6}$ alkyl, ring substituted phenyl $C_{1-6}$ alkyl, e.g., benzyl, 4-methoxybenzyl, 4-nitrobenzyl (pnitrobenzyl), 2-nitrobenzyl (o-nitrobenzyl), and triphenylmethyl (trityl), methoxymethyl, 2,2,2-trichloroethoxycarbonyl, benzyloxymethyl, $C_{1-6}$ alkanoyloxy $C_{1-}$alkyl such as acetoxymethyl, propionyloxymethyl, $C_{2-6}$ alkenyl such as vinyl and allyl. Other suitable carboxy protecting groups well known in the art which have not been disclosed above can be found in "Protective Groups in Organic Synthesis", Theodora W. Greene (John Wiley & Sons, 1981), Chapter 5 incorporated herein by reference. Particularly advantageous carboxy protecting groups are benzyl, p-nitrobenzyl, o-nitrobenzyl, 2,4-dimethoxybenzyl, 4-methoxybenzyl, allyl, substituted allyl, t-butyl or diphenylmethyl (DMP).

Conventional amino protecting groups are also well-known to those skilled in the art and have reference to groups commonly employed in protecting or blocking the amino functional group during a reaction step and which can be split off subsequently without destroying or substantially altering the remaining portion of the molecule. Examples include vinyl, allyl, t-butoxycarbonyl, benzyl, benzyloxycarbonyl, 2-nitrobenzyl, 4-nitrobenzyl, 2-nitrobenzyloxylcarbonyl, formyl, benzoyl, acetyl, ethylcarbonyl, chloroacetyl, trichloroacetyl, trifluoroacetyl, methoxycarbonyl, allyloxycarbonyl, trimethylsilyl, triethylsilyl, triphenylsilyl, t-butyl-dimethylsilyl, methyldiphenylsilyl, 2,4-dimethoxybenzyl, 2,4-dimethoxybenzyloxycarbonyl, 4-methoxybenzyl, 4-(methoxymethoxy)phenyl, bis-(4-methoxyphenyl)-methyl, t-butoxycarbonylmethyl, allyoxycarbonylmethyl, methoxymethyl, methylthiomethyl, methoxyethoxymethyl, 2-(trimethylsilyl)ethoxy]methyl or 2-(methylthiomethoxy)ethoxycarbonyl. In general, amino protecting groups which are readily removed under acid conditions or catalytic hydrogenolysis are preferred, e.g. t-butoxycarbonyl, benzyloxycarbonyl and triphenylmethyl. Other suitable amino protecting groups well known to those skilled in the art can be found in "Protective Groups in Organic Synthesis", Theodora W. Greene (John Wiley & Sons, 1981), Chapter 7, incorporated herein by reference.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, benzyl, 4-methoxybenzyl, indanyl, phthalidyl, methoxymethyl, $C_{1-6}$ alkanoyloxy $C_{1-6}$ alkyl, e.g. acetoxymethyl, pivaloyloxymethyl or propionyloxymethyl, $C_{1-6}$ alkoxycarbonyloxy $C_{1-6}$ alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other physiologically hydrolyzable esters known and used in the penicillin and cephalosporin arts. Such esters are prepared by conventional techniques known in the art.

The structural formulae as drawn herein are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulas represent all tautomeric forms, insofar as they may exist.

The above mentioned compounds also could have several asymmetric carbon atoms and thus could exist in several stereochemical forms. The instant processes are intended to be applicable to a mixture of isomers and to a single stereoisomer. However, in the instant allenylazetidinones, the 3R and 4R configurations are preferred on the azetidinone rings. Further, the 6R and 7R configurations are preferred on cephems of formulas II and III. Moreover, when $R^a$ is of the radical

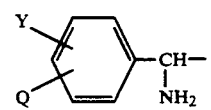

the "D" configuration at the benzylic carbon is preferred.

Besides the tautomeric and asymmetric stereoisomerisms which may exit in the compounds of the present application, there can be "syn" (Z) and "anti" (E) stereoisomerism arising from different orientations of substituent(s) on a double bond. Unless otherwise explicitly stated, the present processes can be applied to a pure isomer and to a mixture of "syn" and "anti" isomers. For example, when a compound of formula I, II or III has an oximino radical substituted with an aminothiazolyl or aminothiadiazolyl ring represented by the formula

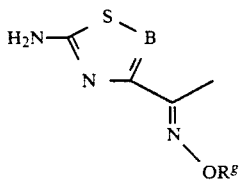

as $R^a$, and in which B and $R^g$ are as previously defined, the imino group has either the "syn" (Z) or "anti" (E) configuration. The radical is drawn as the "syn" isomer. The processes which involve the oximino radicals with at least 90% of the "syn" isomers are preferred. Preferably the above-mentioned radicals are the "syn" isomers which is essentially free of the correspoinding "anti" isomers.

DESCRIPTION OF SPECIFIC EMBODIMENT

A compound of formula I in Scheme (A) can be made by a process depicted in Scheme (G).

In scheme (G), $R^1$, $R^2$, $R^3$ and n are defined previously. A penam sulfoxide of formula XVII are either known or can be made from known processes well established in the art. The conversion of a penam sulfoxide XVII to a dithioazetidione enol of formula XIX can be effected by various processes as disclosed, for example, in *Tetrahedron Letters*, No. 32, pp 3001-3004 (1973), U.S. Pat. Nos. 4,255,328, 4,550,162, or 4,798,890 or in the references cited therein.

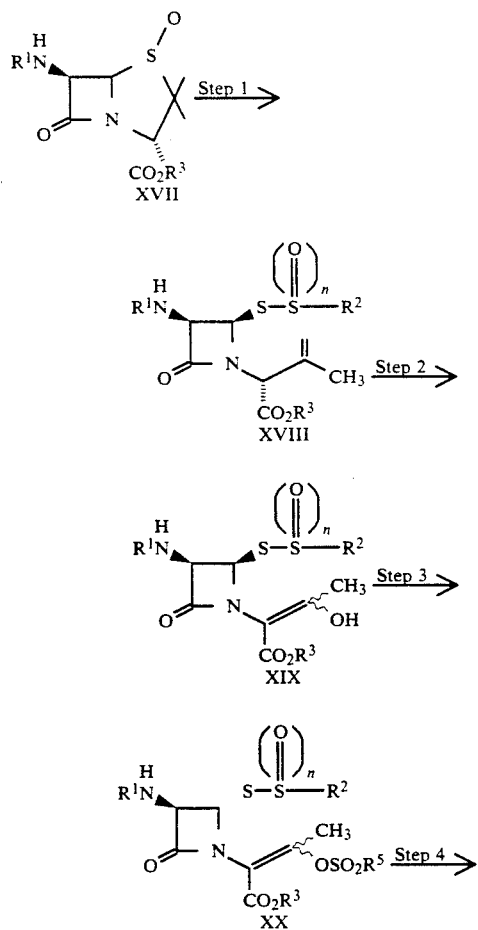

(G)

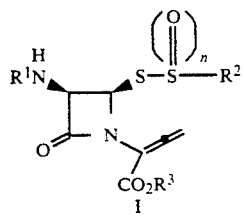

I

The general process to transform an enol of formula XIX into a sulfonic ester formula XX is well described in U.S. Pat. No. 4,550,162. More specifically, compounds of formula XIX is esterified with a reactive functional derivative of a sulphonic acid of the formula HO—$SO_2$—$R^5$, wherein $R^5$ is $C_{1-6}$ alkyl or halogen substituted $C_{1-6}$ alkyl, halogen, aryl, or —$NO_2$ substituted phenyl. Most preferably, $R^5$ is a group selected from $CH_3$, F, $CF_3$, 4-nitrophenyl and 4-methylphenyl. The reactive functional derivatives of a sulphonic acid of the formula HO—$SO_2$—$R^5$ which are used are, for example, their reactive anhydrides, especially the mixed anhydrides with hydrogen halide acids, for example their chlorides, such as mesyl chloride and p-toluenesulphonic acid chloride. Straight anhydrides can also be used such as fluorosulfonic anhydride. The esterification is carried out, preferably in the presence of an organic tertiary nitrogen base, such as pyridine, triethylamine, N,N-diisopropyl-N-ethylamine (diisopropylethylamine), in a suitable inert solvent, such as aliphatic, cycloaliphatic or aromatic hydrocarbon, such as hexane, cyclohexane, benzene or toluene, a halogenated aliphatic hydrocarbon, for example methylene chloride, or an ether, such as a di-($C_{1-6}$) alkyl ether, for example diethyl ether, or a cyclic ether, for example tetrahydrofuran or dioxane, or in a solvent mixture.

The elimination of the sulfonyl leaving group in Step 4 is achieved with a base. Examples of suitable bases for the elimination are organic nitrogen-containing bases, such as tertiary heterocyclic bases of aromatic character, and above all tertiary aliphatic, azacycloaliphatic or araliphatic bases: such as N,N,N-tri-$C_{1-7}$ alkylamines, for example, N,N,N-trimethylamine, N,N-dimethyl-N-ethylamine, N,N,N-triethylamine or N,N-diisopropyl-N-ethylamine; N-$C_{1-7}$ alkyl-azacycloalkanes, for example N-methylpiperidine or N-phenyl-$C_{1-7}$ alkyl-N,N-di-$C_{1-7}$ alkylamines, for example, N-benzyl-N,N-dimethylamine, as well as mixture thereof, such as the mixture of a base of the pyridine type, for example, pyridine and a N,N,N-tri-$C_{1-7}$ alkylamine, for example, pyridine and triethylamine.

Step 1 of Scheme (A) can be effected with a metal halide selected from $ZnCl_2$, $ZnBr_2$, LiCl, LiBr, LiI, $MgCl_2$, $MgBr_2$, $HgCl_2$ and boron and aluminum and cadmium halides (Cl and Br). Preferably, the metal halide is selected from LiCl and LiBr. Any relatively polar solvents which do not interfere with the cyclization can obviously be employed. Preferable solvent of the reaction is tetrahydrofuran or N-methyl pyrrolidinone (1-methyl-2-pyrrolidinone). The cyclization can be achieved in the temperature range of 50° C. to −40° C. However in order to minimize the formation of the $\Delta^2$-isomers, preferable cyclization temperature is between is between −40° C. and 0° C.

Step 2 of Scheme (A) is effected with at least an equimolar amount of $R^4$-tri-$C_{1-6}$ alkylstannane in the presence of about 1-10 mole % of Pd (0) or Pd (II)

compound and furthermore preferably in the presence of about 3-30 mole % of a phosphine reagent and at least an equimolar amount of a metal halide.

The desirable solvent used in Step 2 of Scheme (A) is aprotic and relatively polar. Thus, the solvent may be selected from 1-methyl-2-pyrrolidinone, tetrhydrofuran (THF), nitriles such as acetonitrile, dimethylsulfoxide (DMSO), dimethylformamide (DMF), ethers such as glyme and dioxane, hexamethylphosphoric amide (HMPA), acetone, nitromethane and nitrobenzene. Preferably, the solvent is selected from 1-methyl-2-pyrrolidinone (N-methyl pyrrolidinone), THF, acetonitrile, DMSO and DMF. More preferably, the solvent is selected from N-methyl pyrrolidinone, THF and acetonitrile. Most preferably, the solvent is THF or N-methyl pyrrolidinone.

The phosphine reagent may be selected from phosphine compounds such as, for example, triphenylphosophine, tri-(3-fluorophenyl)phosphine, tri-(3-chlorophenyl)phosphine, tri-(3-methoxyphenyl)phosphine, diphenylmethylphosphine, dimethylphenylphosphine, tributylphosphine, tri-(2-thienyl)-phosphine, and tri-(2-furyl)phosphine. Phosphite compounds such as, for example, trimethyl and triethyl and triphenyl and triisopropyl phosphites may be substituted for the above-mentioned phosphine compounds. Also, chelating phosphines such as, for example, bis-diphenylphosphinoethane and bis-diphenylphosphinopropane may be substituted for the above phosphines. Preferably, the phosphine reagent is tri-(2-furyl)-phosphine or triphenylphosphine.

Although any Pd (palladium) compound may be used in the process of this invention, preferably the Pd compound is selected from a palladium (0) compound such as bis(dibenzylidene acetone)palladium [Pd(dba)$_2$] and a Pd (II) compound such as Pd(OAc)$_2$ and PdCl$_2$.

The metal halide used in combination with the palladium compound in the process according to this invention is selected from ZnCl$_2$, ZnBr$_2$, LiCl, LiBr, LiI, MgCl$_2$, MgBr$_2$, HgCl$_2$ and boron and aluminum and cadmium halides (Cl and Br). Preferably, the metal halide is selected from ZnCl$_2$ and ZnBr$_2$, most preferably, ZnCl$_2$.

Needless to say that in carrying out the steps described in either Scheme (A) or (G), when R$^1$ is an acyl group as defined previously and if such acyl group contains one or more free amino, hydroxy and/or carboxy groups, such groups may be protected with conventional amino, hydroxy and/or carboxy protecting groups. Similarly when COOR$^3$ is a physiologically hydrolyzable ester and if such physiologically hydrolyzable ester contains one or more free amino, hydroxy and/or carboxy groups, such groups may also be protected with conventional amino, hydroxy and/or carboxy protecting groups.

As used herein, conventional hydroxy protecting groups which can be employed in the present invention to block or protect the hydroxy function are well-known to those skilled in the art and, preferably, said groups can be removed, if desired, by methods which do not result in any appreciable destruction of the remaining portion of the molecule, for example by chemical or enzymatic hydrolysis. Examples of such readily removable hydroxy protecting groups include methoxymethyl, 2,2,2-trichloroethyoxymethyl, tetrahydropyranyl, tetrahydrofuranyl, t-butyl, benzyl, p-methoxybenzyl, diphenylmethyl, trialkylsilyl, triphenylsilyl, and the like. Other suitable protecting groups are disclosed in "Protecting Groups in Organic Synthesis", Theodora W. Greene (John Wiley & Sons, 1981), Chapter 2 for hydroxy, which is hereby incorporated by reference.

The specific examples which follow illustrate the synthesis of representative compounds of the instant invention and are not construed as limiting the invention in sphere or scope. The methods may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), broad triplet (br t), broad quartet (br q), singlet (s), multiplet (m), doublet (d), quartet (q), triplet (t), doublet of doublet (dd), doublet of triplet (dt), and doublet of quartet (dq). The solvents employed for taking NMR spectra are DMSO-d$_6$ (perdeuterodimethysulfoxide), D$_2$O (deuterated water), CDCl$_3$ (deuterochloroform) and other conventional deuterated solvents. The infrared (IR) spectral description include only absorption wave numbers (cm$^{-1}$) having functional group identification value. When used in reference to an infrared spectrum, s refers to sharp and vs refers to very sharp.

Celite is a registered trademark of the Johns-Manville Products Corporation for diatomaceous earth.

Except otherwise indicated, ether normally refers to diethyl ether.

The abbreviations used herein are conventional abbreviations widely employed in the art. Some of which are:

FAB: Fast Atom Bombardment
DMSO: dimethyl sulfoxide
Boc: t-butoxycarbonyl
DPM: diphenylmethyl
Ph: phenyl
tBu: t-butyl
HPLC: High pressure liquid chromatography
PNB: 4-nitrobenzyl
Tf: trifluoromethanesulfonyl

EXAMPLE 1

Diphenylmethyl 2-[(3R, 4R)-4-(benzothiazol-2-yl)dithio-3-phenoxyacetamido-2-oxo-azetidin-1-yl]-3-methyl-3-butenoate (XVIIIa)

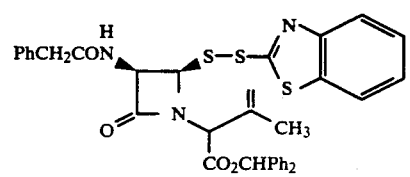

To a solution of diphenylmethyl penicillin V oxide (11.53 g, 0.0223 mole) in toluene (120 mL), 2-mercaptobenzothiazole (3.8 g, 0.0227 mole) was added and the mixture refluxed through a Dean-Stark trap. After 2.5 h, no starting material was detected by thin-layer chromatography. The solution was cooled, filtered through charcoal and Celite, concentrated to a volume of 30-40 mL and cooled to 0° C. Ether (40-50 mL) was added slowly; the crystalline precipitate was filtered and washed with a small portion of cold ether, and then dried in vacuo to afford 12.43 g (83.7%) of the title compound.

ANALYTICAL DATA $^1$H-NMR (CDCl$_3$, 360 MHz) δ 7.8 (d, 1H), 7.6 (d, 1H), 7.5–7.1 (m, 15H), 6.98 (t, 1H), 6.94 (d overlapping s, 3H overall), 5.6 (d, J=5.0 Hz, 1H), 5.42 (dd, J=5.0; 7 Hz, 1H), 5.1 (s, 1H), 5.05 (s, 1H), 4.9 (s, 1H), 4.5 (dd, 2H), 1.95 (s, 3H).

EXAMPLE 2

Diphenylmethyl 2-(3R, 4R)-4-(o-toluenesulfonylthio)-3-phenoxyacetamido-2-oxo-azetidin-1-yl]-3-methyl-3-butenoate (XVIIIb)

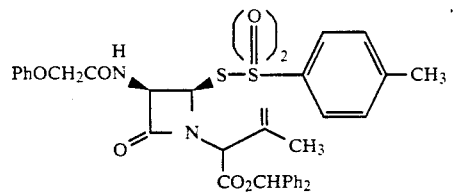

To a solution of diphenylmethyl 2-[(3R,4R)-4-[(benzothiazol-2-yl)dithio]-3-phenoxyacetamido-2-oxo-azetidin-1-yl]-3-methyl-3-butenoate (XVIIIa, 12.12 g, 0.0182 mole) in acetone (325 mL) and water (37 mL), silver nitrate (3.86 g, 0.0227 mole) was added all at once. A freshly prepared solution of sodium p-toluenesulfinate hydrate (4.05 g; 0.0227 mole) in acetone (255 mL) and water (37 mL) was added dropwise over 1 h, while the reaction mixture was protected from light. After an additional 1 h-period at room temperature, Celite (5 g) was added and the mixture was diluted with acetone (500 mL) and then was filtered. The filtrate was evaporated to a small volume, and the crude product was extracted into ether (3×250 mL). The ether phase was dried with magnesium sulfate and concentrated to afford a crude product. Flash chromatography (SiO$_2$, eluting with 40% ethyl acetate in hexane) gave 9.05 g (73.5%) of the title compound as a white solid.

ANALYTICAL DATA $^1$H-NMR (CDCl$_3$ 360 MHz) δ 7.62 (d, 2H), 7.35–7.00 (m, 15H), 6.85 (d, 2H), 5.90 (d, J=5 Hz, 1H), 5.22 (dd, J=5; 7 Hz, 1H), 4.90 (s, 1H), 4.79 (s, 1H), 4.41 (s overlapping dd, 3H overall), 2.32 (s, 3H), 1.80 (s, 3H).

EXAMPLE 3

4-Nitrobenzyl 2-(3R,4R)-4-[(benzothiazol-2-yl)dithiol-3-phenoxyacetamido-2-oxo-azetidin-1-yl]-3-methyl-3-butenoate (XVIIIc)

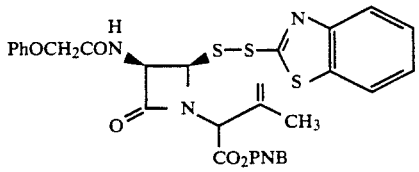

To a solution of 4-nitrobenzyl penicillin V oxide (4.73 g, 0.010 mole) in toluene (100 mL), 2-mercaptobenzothiazole (1.67 g, 0.010 mole) was added and the mixture refluxed through a Dean-Stark trap until no starting material was detected by thin-layer chromatography (4 h). The toluene solution was cooled, the volume was reduced until some precipitation occurred, and the crystallization was allowed to proceed at 0° C. overnight.

Yield: 4.98 g (80%) of the title compound, XVIIIc, as off-white crystals.

ANALYTICAL DATA $^1$H-NMR (CDCl$_3$, 360 MHz) δ 8.18 (d, 2H), 7.8 (d, 1H), 7.6 (d, 1H), 7.5–7.2 (m, 7H), 7.0 (t, 1H), 6.92 (d, 2H), 5.58 (d, 1H), 5.48 (dd, 1H), ca 5.2 (m, 2H+1H), 5.02 (s, 2H), 4.58 (m, 2H), 1.98 (s, 3H).

EXAMPLE 4

4-Nitrobenzyl 2-[(3R,4R)-4-(o-toluenesulfonylthio)-3-phenoxyacetamido-2-oxo-azetidin-1-yl]-3-methyl-3-butenoate (XVIIId)

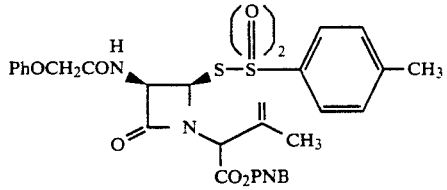

A suspension of 4-nitrobenzyl 2-[(3R,4R)-4-[(benzothiazol-2-yl)dithio]-3-phenoxyacetamido-2-oxo-azetidin-1-yl]-3-methyl-3-butenoate (XVIIIc, 3.25 g, 0.005 mole) in acetone (90 mL) and water (10 mL) was treated at room temperature with silver nitrate (1.06 g, 0.00625 mole), followed by treatment with a solution of sodium p-toluenesulfinate hydrate (0.90 g, 0.050 mole) in acetone (70 mL)—water (10 mL). The slurry was stirred for 1 h at room temperature under darkness. It was then filtered through Celite, which was washed with acetone. The volume of the filterate was reduced in vacuo, and the product was extracted into ether (3×250 mL). The ether phase was dried over magnesium sulfate and concentrated. Flash chromatography (silica gel, 50% ethyl acetate in hexane) gave the pure title product, XVIIId, as a solid (2.053 g, 62%).

ANALYTICAL DATA $^1$H-NMR (CDCl$_3$, 360 MHz): δ 8.22 (d, 2H), 7.7 (d, 1H), 7.6 (d, 1H), 7.4–7.2 (m, 6H), 7.04 (m, 1H), 7.01 (t,

1H), 6.94 (d, 2H), 5.8 (d, J=5 Hz, 1H), 5.30 (dd, 1H), 5.26 (m, 2H), 4.99 (s, 1H), 4.91 (s, 1H), 4.78 (s, 1H), 4.42 (dd, 2H), 2.38 (s, 3H), 1.92 (s, 3H).

EXAMPLE 5

Diphenylmethyl 2-(3R,4R)-4-(p-toluenesulfonylthio)-3-phenoxyacetamido-2-oxo-azetidin-1-yl]-3-hydroxy-2-butenoate (XIXa)

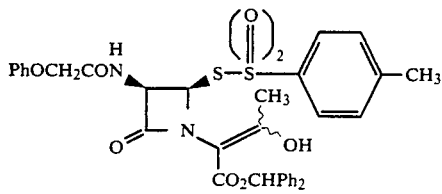

A solution of diphenylmethyl 2-[(3R,4R)-4-(p-toluenesulfonylthio)-3-phenoxyacetamido-2-oxo-azetidin-1-yl]-3-methyl-3-butenoate (XVIIIb) (9.00 g, 0.0135 mole) in methyl acetate (250 mL) was cooled to −78° C. and dry ozone was gently bubbled through the solution until a pale blue endpoint was obtained (40 min.). Nitrogen gas was passed through the solution until it became colorless. Subsequently, methylsulfide (15 mL) was added at once, and the solution was allowed to reach 0° C. over the course of 2 h. The crude product, obtained by evaporation of the solvent, was purified by silica gel flash chromatography (50% ethyl acetate in hexane) to yield 8.378 g (91.5%) of the title product as a colorless foam.

ANALYTICAL DATA $^1$H-NMR (CD$_2$Cl$_2$, 360MHz) δ 11.8 8(br s, 1H), 7.5–6.9 (m, 19H), 6.85 (s, 1H), 5.75 (d, 1H), 5.1(q, 1H), 4.55 (m, 2H), 2.39 (s, 3H), 2.0 (s, 3H).

EXAMPLE 6

4-Nitrobenzyl 2-[(3R,4R)-4-(benzothiazol-2-yl)dithio]-3-phenoxyacetamido-2-oxo-azetidin-1-yl]-3-hydroxy-2-butenoate (XIXb)

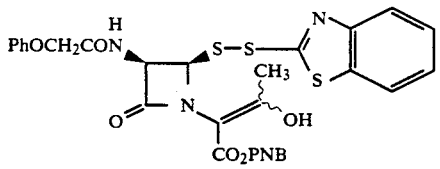

A solution of 4-nitrobenzyl 2-[(3R,4R)-4-[(benzothiazol-2-yl)dithio]-3-phenoxyacetamido-2-oxo-azetidin-1-yl]-3-methyl-3-butenoate (XVIIIc, 1.52 g, 0.00244 mole) in 2:1 methanol/dichloromethane (165 mL), at −78° C., was treated with a stream of dry ozone until a pale blue coloration was reached (10 min). Nitrogen was then bubbled through the solution to discharge the blue color and methyl sulfide (1.5 mL) was added. The solution was allowed to reach 0° C. over the course of 2 h. Evaporation of the solvents gave a crude product which was purified by flash-chromatography over silica gel (65% ethyl acetate in hexane) to yield 1448 g (95%) of the title compound, XIXb, as a white foam.

ANALYTICAL DATA $^1$H-NMR (CDCl$_3$, 360 MHz): δ 12.2 (br s, 1H), 8.01 (d, 2H), 7.82 (d, 1H), 7.61 (d, 1H), 7.5–7.2 (m, 7H), 7.01 (t, 1H), 6.98 (d, 2H), 5.39 (d, J=5 Hz, 1H), 5.25–5.0 (m, 3H), 4.6 (m, 2H), 2.36 (s, 3H).

EXAMPLE 7

4-Nitrobenzyl 2-[(3R,4R)-4-(p-toluenesulfonylthio)-3-phenoxyacetamido-2-oxo-azetidin-1-yl]-3-hydroxy-2-butenoate (XIXc)

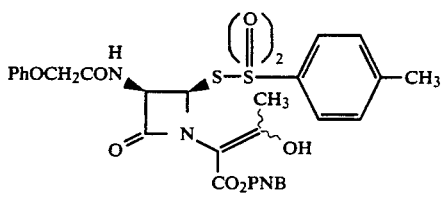

A solution of 4-nitrobenzyl 2-[(3R,4R)-4-(p-toluenesulfonylthio)-3-phenoxyacetamido-2-oxo-azetidin-1-yl]-3-methyl-3-butenoate (XVIIId, 1.13 g, 0.00178 mole) in methyl acetate (30 mL) was treated at −78° C. with a slow stream of ozone until a blue coloration persisted (10 min). Nitrogen was used to sweep the excess ozone. Subsequently, methylsulfide (2 mL) was added and the temperature was allowed to reach 0° C. over the course 4 h. Evaporation of the solvent and flash chromatography of the residue (silica gel, 60% ethyl acetate in hexane) gave 1.09 g (96.3%) of the pure title product, XIXc, as a foam.

EXAMPLE 8

Diphenylmethyl 2-[(3R,4R)-4-(p-toluensulfonylthio)-3-phenoxyacetamido-2-oxo-azetidin-1-yl]-3-trifluoromethanesulfonyloxy-2-butenoate (XXa)

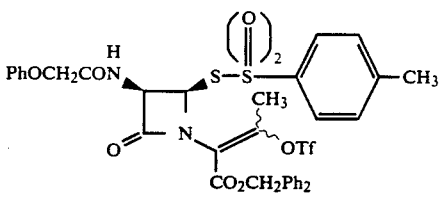

Embodiment a: To a solution of diphenylmethyl 2-[(3R,4R)-4-(p-toluenesulfonylthio)-3-phenoxyacetamido-2-oxo-azetidin-1-yl]-3-hydroxy-2-butenoate (XIXa, 8.35 g, 0.0123 mole) in dry dichloromethane (80 mL), cooled to −78° C., was added triflic (trifluoromethanesulfonic) anhydride (2.60 mL, 0.015 mole) and followed by diisopropylethylamine (2.70 mL, 0.015 mole) rather quickly with vigorous stirring of the solution. After 1 h at −78° C., dilute hydrochloric acid (0.05N, 200 mL) was added and the cooling bath was removed. The product was extracted into ethyl acetate (500 mL). The ethyl acetate phase was first washed twice with dilute hydrochloric acid and then twice with water, dried over magnesium sulfate, and concentrated. Flash silica gel chromatography (40% ethyl acetate in hexane) gave 8.82 g (86.5%) of the title product as a white foam.

ANALYTICAL DATA

¹H-NMR (CDCl₃, 360 MHz) δ 7.5-7.0 (m, 18H), 6.98 (s, 1H), 6.82 (d, 2H), 5.90 (d, 1H), 5.00 (dd, 1H), 4.48 (m, 2H), 2.32 (s, 6H).

Embodiment b: To a solution of 4.75 g (7.06 mmol) of diphenylmethyl 2-[(3R,4R)-4-(p-toluenesulfonylthio)-3-phenoxyacetamido-2-oxo-azetidin-1-yl]-3-hydroxy-2-butenoate (XIXa) in 40 mL of dry dichloromethane at −78° C. (dry-ice/acetone) was added, dropwise, 1.53 mL (8.82 mmol) of diisopropylethylamine followed by 1.48 mL (8.82 mmol) of trifluoromethanesulfonic anhydride. The reaction mixture was stirred at −78° C. under an atmosphere of argon for 30 min. After completion of the reaction, as indicated by tlc (thin layer chromatography), the orange solution was quenched with ice-water. The aqueous layer was extracted with dichloromethane (20 mL), and the combined organic layers were washed with brine (10 mL), 10% HCl solution (10 mL), water (5 mL), dried (magnesium sulfate), and concentrated in vacuo to give a yellow colored oil. Flash chromatography of the oil using hexanes-ethyl acetate (1:1) afforded 4.89 g (86%) of the title product as a white foam.

EXAMPLE 9

4-Nitrobenzyl 2-[(3R,4R)-4-[(benzothiazol-2-yl)dithio]-3-phenoxyacetamido-2-oxo-azetidin-1-yl]-3-trifluoromethanesulfonyloxy-2-butenoate (XXb)

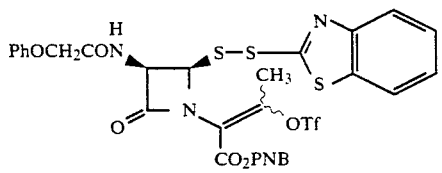

Analogous to a procedure as described in Example 8, 0.144 g (0.000230 mole) of 2-[(3R,4R)-4-[(benzothiazol2-yl)dithio]-3-phenoxyacetamido-2-oxo-azetidin-1-yl]-3-hydroxy-2-butenoate (XIXb), was converted to 0.152 g (87.3%) of the title triflate, XXb, as a white foam after flash chromatography (silica gel, 40% ethyl acetate in hexane).

ANALYTICAL DATA

¹H-NMR (CDCl₃, 360 MHz): δ 8.01 (d, 2H), 7.83 (d, 1H), 7.7 (d, 1H), 7.5-7.2 (m, 7H), 7.03 (t, 1H), 6.97 (d, 2H), 5.72 (d, J=5 Hz, 1H), ca. 5 (m, 3H), 4.61 (m, 2H), 2.55 (s, 3H).

MASS (FAB, GLYCEROL): 785 (M++1).

EXAMPLE 10

4-Nitrobenzyl 2-[(3R,4R)-4-(o-toluenesulfonylthio)-3-phenoxyacetamido-2-oxo-azetidin-1-yl]-3-methanesulfonyloxy-2-butenoate (XXc)

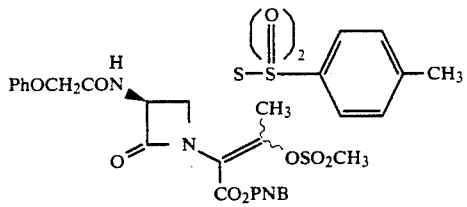

A solution of 4-nitrobenzyl 2-[(3R,4R)-4-(p-toluenesulfonylthio)-3-phenoxyacetamido-2-oxo-azetidin-1-yl]-3-hydroxy-2-butenoate (XIXc, 0.131 g, 0.000206 mole) in dry dichloromethane (3 mL) at −78° C. was treated with triethylamine (0.031 ml, 0.00022 mole) and methanesulfonyl (mesyl) chloride (0.0175 mL, 0.00022 mole), and the temperature was allowed to reach −20° C. over the course of 3 h. Another portion of triethylamine (0.031 mL, 0.00022 mole) and mesyl chloride (0.0175 mL, 0.00022 mole) was added and, after a further 1 h period at −20° C., the brown solution was quenched with dilute hydrochloric acid and extracted with ethyl acetate. The organic phase was washed with dilute acid (0.05N HCl) followed by brine and dried over magnesium sulfate. Flash chromatography (silica gel, 50–60% ethyl acetate in hexane) gave the title product, XXc, as a mixture of E and Z isomers in 1:1 ratio and as a colorless foam. Yield: 0.122 g (83%).

ANALYTICAL DATA

¹H-NMR (CDCl₃, 360 MHz): δ 8.25–8.20 (2xdd, 2H), 7.6–6.8 (m, 12 H), 5.95 (d, J=5.3 Hz, 0.5H), 5.90 (d, J=5.3 Hz, 0.5H), 5.33 (m, 2H), 5.18 (dd; J=5.3, 6.5 Hz; 0.5H), 5.05 (dd; J=5.3, 6.5 Hz; 0.5 H), 4.5–4.4 (m, 2H), 3.31 (s, 1.5H), 3.18 (s, 1.5H), 2.6 (s, 1.5 H), 2.42 (s, 1.5H), 2.41 (s, 1.5H), 2.40 (s, 1.5 H).

EXAMPLE 11

Diphenylmethyl 2-(3R,4R)-4-(benzothiazol-2-yl)dithio]-3-phenoxyacetamido-2-oxo-azetidin-1-yl]-3-fluorosulfonyloxy-2-butenoate (XXd)

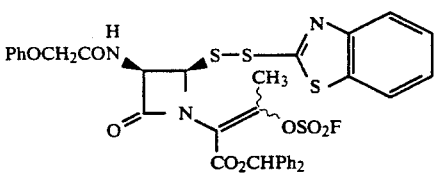

To a solution of 5.0 g (7.32 mmol) of diphenylmethyl 2-[(3R, 4R)-4-[(benzothiazol-2-yl)dithio]-3-phenoxyacetamido-2-oxo-azetidin-1-yl]-3-hydroxy-2-butenoate in 20 mL of dry dichloromethane at −78° C. (dry ice-/acetone) was added dropwise 1.40 mL 8.05 mmol) of diisopropylethylamine followed by 1.86 mL (10.24 mmol) of fluorosulfonic anhydride. The reaction mixture was stirred at −78° C. under an atmosphere of argon for 2.5 h before quenching with water (50 mL). The organic layer was separated. It was further washed with brine (15 mL), 10% HCl solution (15 mL), and water (15 mL), and dried (magnesium sulfate) and concentrated in vacuo to give a light yellow foam. The foam was further purified by flash chromatography (silica, 45% ethyl acetate in hexanes) to afford 4.6 g (84%) of the title compound.

ANALYTICAL DATA

IR (KBr) 1788, 1733, 1630 cm−1.

$^1$H NMR (CDCl$_3$) δ 2.56 (s, 3H), 4.62 (ABq, J=18.9 and 37.8 Hz, 2H), 5.06 (dd, J=5.6 and 7.5 Hz, 1H), 5.57 (d, J=5.6 Hz, 1H), 6.83 (s, 1H), 6.92 (d, J=7.8 Hz, 1H), 6.98–7.83 (m, 19H)

HRMS (high resolution mass spec) calcd for C$_{35}$H$_{28}$FN$_3$O$_8$S$_4$ 766.0822, found 766.0846.

EXAMPLE 12

Diphenylmethyl 2-(3R, 4R)-4-(o-toluenesulfonylthio)-3-phenoxyacetamido-2-oxo-azetidin-1-yl]-3-fluorosulfonyloxy-2-butenoate (XXe)

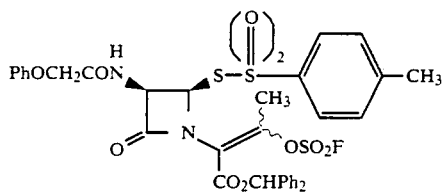

To a solution of 10.0 g (14.86 mmol) of diphenylmethyl 2-[(3R, 4R)-4-(p-tolueneulfonylthio)-3-phenoxyacetamido-2-oxo-azetidin-1-yl]-3-hydroxy-2-butenoate (XIXa) in 90 mL of dry dichloromethane at −78° C. (dry ice/acetone) was added, dropwise, 2.84 mL (16.34 mmol) of diisopropylethylamine followed by 1.69 mL (16.34 mmol) of fluorosulfonic anhydride. The reaction mixture was stirred at −78° C. under an atmosphere of argon for 2.5 h before quenching with water (50 mL). The organic layer was separated. It was further washed with brine (15 mL), 10% HCl solution (15 mL), and water (15 mL), dried (magnesium sulfate), and concentrated in vacuo to give a light yellow foam. The foam was purified further by flash chromatography (silica, 45% ethyl acetate in hexanes) to afford 9.18 g (82%) of the title product.

ANALYTICAL DATA

IR (KBr) 1795, 1716, 1684 cm−1.

$^1$H NMR (CDCl$_3$) δ §2.30 (s, 3H), 2.42 (s, 3H), 4.50 (d, J=2.8 Hz, 2H), 5.05 (dd, J=5.5 and 7.3 Hz, 1H), 5.99 (d, J=5.3 Hz, 1H), 6.88 (d, J=7.8 Hz, 1H), 6.93 (s, 1H), 7.00–7.50 (m, 19H).

HRMS (high resolution mass spec) calcd for C$_{35}$H$_{31}$FN$_2$O$_{10}$S$_3$ 755.1203, found 755.1202.

Anal. Calcd for C$_{35}$H$_{31}$FN$_2$O$_{10}$S$_3$: C, 55.53; H, 4.42; N, 3.70. Found. C, 55.29; H, 4.15; N, 3.63.

EXAMPLE 13

Diphenylmethyl 2-[(3R, 4R)-4-[(benzothiazol-2-yl)dithio]3-phenylacetamido-2-oxo-azetidin-1-yl]-3-fluorosulfonyloxy-2-butenoate (XXf)

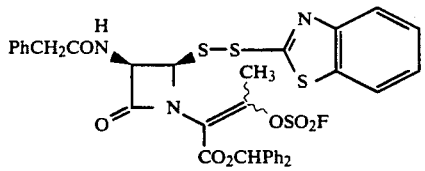

Under a stream of dry nitrogen, the flask was charged with 2.51 g (3.76 mmol) of diphenylmethyl 2-[(3R, 4R)-4-[(benzothiazol-2-yl)dithio]-3-phenylacetamido-2-oxo-azetidin-1-yl]-3-hydroxy-2-butenoate and 45 mL of dry dichloromethane. To the resulting solution at −78° C. was added 0.56 mL (3.95 mmol) of triethylamine followed by 0.41 mL (3.95 mmol) of fluorosulfonic anhydride. After 45 min, the reaction mixture was poured into water (50 mL). The organic phase was separated and washed with water (50 mL) and brine (50 mL). It was further dried (magnesium sulfate), filtered, and concentrated in vacuo to yield 2.67 g (95%) of the title product as a mixture of Z (major) and E (minor) isomers (6:1).

ANALYTICAL DATA

IR (KBr) 1789, 1718, 1663, cm−1.

$^1$H-NMR (CD$_2$Cl$_2$) (Z-isomer) δ 2.54 (s, 3H), 3.72 (s, 2H), 4.87 (dd, J=5.2, and 7.2 Hz, 1H), 5.51 (d, J=5.2, Hz, 1H), 6.28 (d, J=7.2 Hz, 1H), 6.78 (s, 1H), 7.1–7.5 (m, 17H), 7.72 (d, J=7.8 Hz, 1H), 7.84 (d, J=8.1 Hz, 1H);

$^1$H-NMR (CD$_2$Cl$_2$) (E-isomer, partial spectrum) δ 2.45 (s, 3H), 3.67 (s, 2H), 5.35 (dd, J=5.0 and 8.0 Hz, 1H), 5.49 (d, J=5.0 Hz, 1H), 6.86 (s, 1H).

HRMS calcd for C$_{35}$H$_{28}$FN$_3$O$_7$S$_4$ 750.0872 (M+H+), found 750.0857.

EXAMPLE 14

Diphenylmethyl 2-(3R,4R)-4-(o-toluenesulfonylthio)-3-phenoxyacetamido-2-oxo-azetidin-1-yl]-3-p-toluenesulfonyl-2-butenoate (XXg)

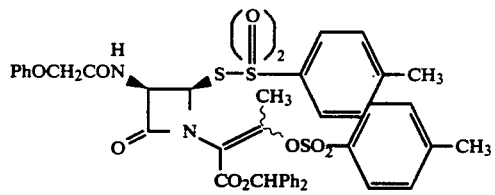

To a solution of 1.0 g (1.48 mmol) of diphenylmethyl 2-[(3R,4R)-4-(p-toluenesulfonylthio)-3-phenoxyacetamido-2-oxo-azetidin-1-yl]-3-hydroxy-2-butenoate (XIXa) was added, dropwise, 283.93 μL (1.63 mmol) of diisopropylethylamine followed by 527.12 mg of p-toluenesulfonic anhydride. The solution was cooled to −78° C. and stirred for 2.0 hr before quenched with ice-water solution (10 mL). The organic layer was separated and washed with water, saturated aqueous NaH- CO₃ solution, brine and 10% HCl solution. After the solution was further dried (MgSO₄) and concentrated, the title compound was isolated as a foam. Further purification by flash chromatography (silica, 50% ethyl acetate in hexanes) afforded 1.04 g (85% yield) of the product. The compound was isolated as a single isomer.

ANALYTICAL DATA

HRMS calcd for $C_{42}H_{39}N_2O_{10}S_3$ 827.1767 (M+H⁺), found 827.1764.

EXAMPLE 15

2-[(3R,4R)-(p-Toluenesulfonylthio)-3-phenoxyacetamido-2-oxo-azetidin-1-yl]-3-o-nitrobenzenesulfonyloxy-2-butenoate (XXh)

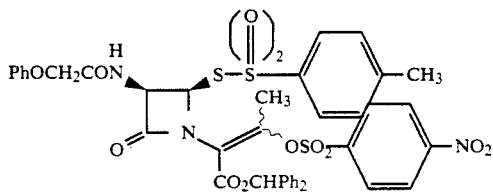

To a solution of 1.0 g (1.48 mmol) of diphenylmethyl 2-[(3R,4R)-4-(p-toluenesulfonylthio)-3-phenoxyacetamido-2-oxo-azetidin-1-yl]-3-hydroxy-2-butenoate (XIXa) in 10 mL dichloromethane at 0° C. was added, dropwise, 246.70 μL (1.77 mmol) of triethylamine followed by 327.9 mg of p-nitrobenzenesulfonyl chloride (1.77 mmol). The reaction mixture was stirred for 2.0 hr at 0° C. before being quenched with an ice-water solution (10 mL). The organic layer was separated and subsequently washed with water, brine, saturated aqueous NaHCO₃ solution, and 10% HCl solution. After the solution was further dried (MgSO₄) and concentrated, 850 mg (67%) of the title compound was isolated as a yellow foam. The compound was not further characterized but was converted to the correponding allene.

EXAMPLE 16

Diphenylmethyl 2-[(3R,4R)-4-(p-toluenesulfonylthio)-3-phenoxyacetamido-2-oxo-azetidin-1-yl]-2,3-butadienoate (Ia)

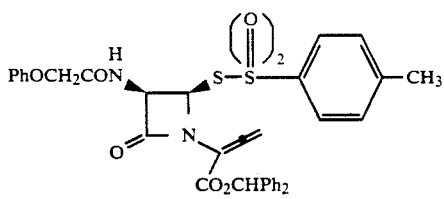

Embodiment a: A solution of diphenylmethyl 2-[(3R,4R)-4-(p-toluenesulfonylthio)-3-phenoxyacetamido-2-oxo-azetidin-1-yl]-3-trifluoromethanesulfonyloxy-2-butenoate (XXa, 0.300 g, 0.00036 mole) in dry tetrahydrofuran (3 mL) was treated with triethylamine (0.077 mL, 0.00036 mole) for 1 h at room temperature. Reverse-phase chromatography (C-18 column, eluting with 65% acetonitrile—35% of 0.01M phosphate pH 6.5 buffer) showed complete consumption of the starting material after 45 min with formation of a single, faster-eluting product. 0.05M sulfuric acid and ethyl acetate was added to the reaction mixture, followed by separating the two phases. The organic phase was dried with sodium sulfate and evaporated to give diphenylmethyl 2-[(3R,4R)-4-(p-toluenesulfonylthio)-3-phenoxyacetamido-2-oxo-azetidin-1-yl]-2,3-butadienoate (Ia) as a colorless foam (0.245 g, quantitative).

ANALYTICAL DATA

¹H NMR (CDCl₃) δ 2.29 (s, 3H), 4.41 and 4.51 (ABq, J=14.7 and 29.4 Hz, 2H) 5.45 (dd, J=5.0 and 8.4 Hz, 1H), 5.60 (d, J=8.4 Hz, 1H), 6.84 (s, 1H), 6.91 (d, J=8.4 Hz, 1H), 7.03 (t, J=7.5 Hz, 1H), 7.16 (d, J=8.4 Hz, 1H), 7.25-7.41 (m, 16H), 7.60 (d, J=8.4 Hz, 1H).

HRMS calcd for $C_{35}H_{30}N_2O_7S_2$ 655.1573 (M+H⁺), found 655.1566.

Anal. Calcd for $C_{35}H_{30}N_2O_7S_2$: C, 64.27; H, 4.77; N, 4.27. Found: C, 64.45; H, 5.07; N, 4.33.

Embodiment b: To a solution of 4.03 g (5.34 mmol) of diphenylmethyl 2-[(3R,4R)-4-(p-toluene-sulfonylthio)-3-phenoxyacetamido-2-oxo-azetidin-1-yl]-3-fluorosulfonyloxy-2-butenoate (XXe) in 20 mL of dry dichloromethane at room temperature was added, dropwise, 788.89 μl (5.66 mmol) of triethylamine. The solution was stirred at ambient temperature for 45 min. HPLC indicated a quantitative formation of the product (retention time=2.68 min; 2.0 ml/min; 60% acetonitrile: 40% of 0.01 M (NH₄)₂HPO₄ buffer, pH=6.5, reversed phase C-18 column). The resultant solution was poured into water. The organic layer was separated and washed with brine (10 mL) and 5% HCl solution (10 mL). It was further dried (magnesium sulfate) and concentrated to give a light yellow foam, which was recrystallized from isopropanol to afford 3.15 g (90%) of the title product.

Embodiment c: To a solution of 25 mg (0.03 mmol) of diphenylmethyl 2-[(3R,4R)-4-(p-toluenesulfonylthio)3-phenoxyacetamido-2-oxo-azetidin-1-yl]-3-p-toluenesulfonyl-2-butenoate (XXo) in 1.0 mL of dry dichloromethane at room temperature was added dropwise, 4.42 μL (0.032 mmol) of triethylamine. The solution was stirred at ambient temperature for 40 min. The reaction mixture was added into water (1.0 mL) and phases were separated. The organic layer was washed with brine (2 mL) and 4% HCl solution (2 mL). It was subsequently dried (magnesium sulfate) and concentrated to afford 16.9 mg (87%) of the desired title product.

Embodiment d: To a solution of 600 mg (0.79 mmol) of diphenylmethyl 2-[(3R,4R)-4-(p-toluene-sulfonylthio)-3-phenoxyacetamido-2-oxo-azetidin-1-yl]-3-methanesulfonyloxy-2-butenoate (XXc) in 6.0 mL of dichloromethane at room temperature was added 110 μL of triethylamine (0.79 mmol). The solution was stirred for 2.0 hours at ambient temperature. The reaction mixture was added into water (2.0 mL) and phases were separated. The organic layer was washed with brine (2 mL), dried (magnesium sulfate) and concentrated to give 445.1 mg (86%) of the desired title product.

Embodiment e: To a solution of 1.0 g (1.24 mmol) of diphenylmethyl 2-[(3R, 4R)-4-(p-toluenesulfonylthio)-3-phenoxyacetamido-2-oxo-azetidin-1-yl]-3-trifluoromethanesulfonyloxy-2-butenoate (XXa) in 10 mL of dichloromethane at room temperature was added triethylamine (0.72 mL, 1.24 mmol). The solution was stirred for 60 min at ambient temperature before being added into water (5.0 mL). The phases were separated. The organic phase was washed with brine (10 mL) and 4% HCl solution (10 mL). It was subsequently dried (magnesium sulfate) and concentrated to afford 0.74 g (90%) of the title product as a foam.

Embodiment f: To a solution of 100 mg (0.11 mmol) of diphenylmethyl 2-[(3R,4R)-(p-toluenesulfonylthio)-3-phenoxyacetamido-2-oxo-azetidin-1-yl]-3-p-nitrobenzenesulfonyloxy-2-butenoate (XXh) in 2.0 mL of dichloromethane at room temperature was added triethylamine (15.49 µl, 0.11 mmol). The solution was stirred at ambient temperature for 45 min before being added into water (2.0 mL). The phases were separated. The organic phase was washed with brine (2 mL) and 4% HCl solution (2 mL). It was subsequently dried (magnesium sulfate) and concentrated to give the title product (62.7 mg, 87%).

EXAMPLE 17

Diphenylmethyl 2-[(3R, 4R)-4-[(benzothiazol-2-yl)dithio1-3-phenoxyacetamido-2-oxo-azetidin-1-yl]-2,3-butadienoate (Ib)

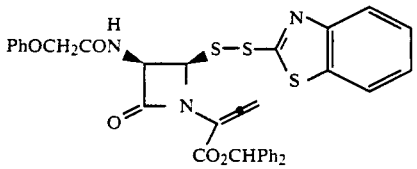

Embodiment a: To a solution of 200 mg (0.261 mmol) of diphenylmethyl 2-[(3R, 4R)-4-[(benzothiazol-2yl)dithio]-3-phenoxyacetamido-2-oxo-azetidin-1-yl]3-fluorosulfonyloxy-2-butenoate (XXd) in 2.0 mL of dry dichloromethane at room temperature was added, dropwise, 38.26 µL (0.274 mmol) of triethylamine. The solution was stirred at ambient temperature for 25 min. HPLC indicated disappearance of the starting material and formation of the product (retention time=4.74 min, 2.0 mL/min, 70% acetonitrile: 30% water, reversed phase C-18 column). The resultant solution was poured into water. The organic layer was separated and further washed with brine (10 mL) and 5% HCl solution (10 mL). It was subsequently dried (magnesium sulfate) and concentrated to give 139.09 mg (81%) of the title product as a light brown foam, which was further purified by recrystallization from isopropanol.

ANALYTICAL DATA $^1$H NMR (CDCl$_3$) δ 4.41 and 4.49 (ABq, J=17.0 and 29.3 Hz, 2H), 5.10 (d, J=15.5 Hz, 1H), 5.60 (dd, J=5.0 and 8.0 Hz, 1H), 5.65 (d, J=15.5 Hz, 1H), 6.83 (s, 1H), 7.60–6.90 (m, 18H), 7.82 (d, J=9.5 Hz, 1H).

Embodiment b: To a solution of 20 mg (0.03 mmol) of diphenylmethyl 2-[(3R, 4R)-4-[(benzothiazol-2-yl)dithio]-3-phenoxyacetamido-2-oxo-azetidin-1-yl]-3-methanesulfonyloxy-2-butenoate in 2.0 mL of dichloromethane at room temperature was added 4.39 µL (0.031 mmol) of triethylamine. The solution was stirred at ambient temperature for 40 min. The reaction mixture was added into water (1.0 mL) and phases were separated. The organic layer was washed with brine (2 mL) and 4% HCl solution (2 mL). It was subsequently dried (magnesium sulfate) and concentrated to afford 14.2 mg (82%) of the title product.

EXAMPLE 18

Diphenylmethyl 2-[(3R, 4R)-4-(benzothiazol-2-yl)dithio1-3-phenylacetamido-2-azetidinon-1-yl]-2,3-butadienoate (Ic)

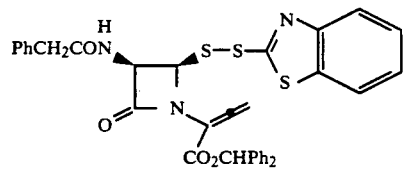

Under a stream of dry nitrogen, the flask was charged with 500 mg (0.65 mmol) of diphenylmethyl 2-[(3R,4R)-4-[(benzothiazol-2-yl)dithio]-3-phenylacetamido-2-oxo-azetidin-1-yl]-3-fluorosulfonyloxy-2-butenoate (XXf) and 5.0 mL of dry THF. After stirring the solution for 15 min at 0°–5° C., 92.0 µL (0.65 mmol) of triethylamine was added dropwise. Stirring at 0°–5° C. under a blanket of dry nitrogen was continued for 2 hr. The solution was diluted with THF (10 mL) and poured into a saturated NaCl solution (30 mL). The phases were separated and the organic phase was dried 15 min over anhydrous MgSO$_4$, filtered and concentrated to a small volume (ca. 6 mL). The solution was added dropwise into 36 mL of hexanes with vigorous stirring. After 30 min, the solid was collected by suction filtration and dried in vacuo for 3 h at 22° C. to yield 387 mg (92%) of the title product as a beige powder.

ANALYTICAL DATA $^1$H NMR (CD$_2$Cl$_2$) δ 3.65 (s, 2H), 5.20 and 5.59 (ABq, J =15.3 Hz, 2H), 5.41 (dd, J=4.8 and 8.0 Hz, 1H), 5.76 (d, J=4.8 Hz, 1H), 6.51 (d, J=8 Hz, 1H), 6.78 (s, 1H), 7.0–7.5 (m, 17H), 7.52 (d, J=7.9 Hz, 1H), 7.81 (d, J=8.4 Hz, 1H).

HRMS calcd for C$_{35}$H$_{27}$N$_3$O$_4$S$_3$ 650.1242, found 650.1244 (M+H+).

EXAMPLE 19

4-Nitrobenzyl 2-[(3R,4R)-4-[(benzothiazol-2-yl)dithio]-3-phenoxyacetamido-2-oxo-azetidin-1-yl]-2,3-butadienoate (Id)

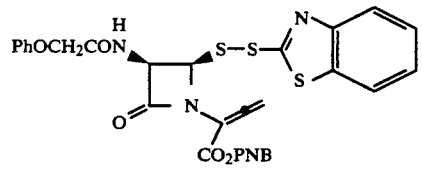

A solution of 4-nitrobenzyl 2-[(3R,4R)-4-[(benzothiazol-2-yl)dithio]-3-phenoxyacetamido-2-oxo-azetidin-1-yl]-3-trifluoromethanesulfonyloxy-2-butenoate (XXb, 0.147 g, 0.000187 mole) in acetonitrile at −40° C. was treated with triethylamine (0.026 mL, 0.000187 mole). A tan precipitate formed. The temperature of the mixture was allowed to reach −10° C. over the course of 1 h, and the suspension was carefully filtered under argon atmosphere. The precipitate was washed with ice-cold acetonitrile (2×2 mL). After drying the solid in vacuo for 30 min at room temperature, the 0.070g (59% yield) of allene Id was obtained. It could be stored at −10° C. for several days, but it was preferably used within 24 h of its preparation.

ANALYTICAL DATA $^1$H-NMR (CDCl$_3$, 360 MHz): δ 8.15 (d, 2H), 7.82 (d, 1H), 7.62 (d, 1H), 7.51 (d, 1H), 7.5–7.2 (m, 6H), 7.0 (t, 1H), 6.94 (d, 2H), 5.80 (d, J=5 Hz, 1H), 5.6 (d+dd, 2H), 5.34 (d, J=17.5 Hz, 1H), 5.12 (dd, 2H), 4.58 (dd, 2H).

IR (KBr cast): cm$^{-1}$ 1950; 1910 (weak).

EXAMPLE 20

4-Nitrobenzyl 2-[(3R,4R)-4-(o-toluenesulfonylthio)-3-phenoxyacetamido-2-oxo-azetidin-1-yl]-2,3-butadienoate (Ie)

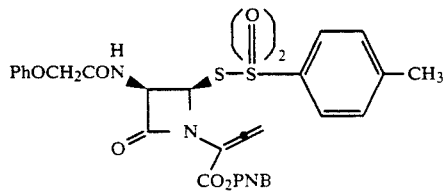

A solution of 4-nitrobenzyl 2-[(3R,4R)-4-(p-toluenesulfonylthio)-3-phenoxyacetamido-2-oxo-azetidin-1-yl]-3-methanesulfonyloxy-2-butenoate (XXc, 0.0714 g, 0.00010 mole) in chloroform (1 mL) was treated with triethylamine (0.014 mL, 0.00010 mole) at room temperature. After a period of 1 h, reverse-phase C-18 HPLC indicated consumption of the starting material with formation of a single new peak (65% acetonitrile and 0.01M phosphate pH 6.5 buffer). Dilute hydrochloric acid (chilled at 0° C.) and ethyl acetate were added. The organic layer was washed with cold water, dried (sodium sulfate) and concentrated to give 0.0615 g (ca 100%) of the title compound as a foam. The product was characterized by its $^1$H-NMR spectrum.

ANALYTICAL DATA $^1$H-NMR (CDCl$_3$, 360 MHz): δ 8.21 (d, 2H), 7.71 (d, 1H), 7.55 (d, 1H), 7.35–7.25 (m, 7H), 7.02 (t, 1H), 6.89 (d, 2H), 5.94 (d, J=5.5 Hz, 1H), 5.80–5.70 (2d's, J=ca. 17.5 Hz, 2H), 5.53 (dd; J=5.5, 7.0 Hz; 1H), 5.32 (m, 2H), 4.45 (m, 2H), 2.40 (s, 3H).

EXAMPLE 21

Diphenylmethyl 7-phenoxyacetamido-3-p-toluenesulfonyl-3-cephem-4-carboxylate (IIa)

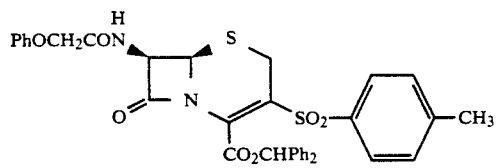

After adding dry N-methyl pyrrolidinone (3 mL) and dry lithium bromide (0.120 g, 0.00138 mole) to diphenylmethyl 2-[(3R,4R)-4-(p-toluenesulfonylthio)-3-phenoxyacetamido-2-oxo-azetidin-1-yl]-2,3-butadienoate (Ia), the resulting mixture was stirred for 16 h at room temperature. Water and ethyl acetate were added (100 mL each) and the two resulting phases were separated. The organic phase was thoroughly washed with water, dried (magnesium sulfate) and concentrated. Crystallization (at −10° C.) of the crude oil from ethyl acetate—hexane gave 0.1498 g (61%) of compound IIa as heavy white crystals, m.p. 192°–3° C. (With considerable gradual darkening).

ANALYTICAL DATA $^1$H-NMR (CDCl$_3$, 360 MHz) δ 7.72 (d, 2H), 7.50–7.1 (m, 14H), 7.1 (s, 1H), 7.0 (t, 1H), 6.88 (d, 2H), 5.92 (dd; J=5.2, 6.8 Hz; 1H), 5.0 (d, J=5.2 Hz, 1H), 4.52 (s, 2H), 3.59 (d, J=17.7 Hz, 1H), 3.38 (d, J=17.7 Hz, 1H), 2.40 (s, 3H).

IR (film) cm$^{-1}$ 1790 (vs), 1750 (s), 1325 (s), 1150 (Vs).

Elem. Anal. Calcd. for C$_{35}$H$_{30}$N$_2$O$_7$S$_2$: C, 64.20; H, 4.62; N, 4.78; S, 9.79.

Found: C, 63.16, H, 4.48; N, 4.48; S, 9.80.

EXAMPLE 22

4-Nitrobenzyl 7-phenoxyacetamido-3-[(benzothiazol-2-yl)dithio]-3-cephem-4-carboxylate (IIb)

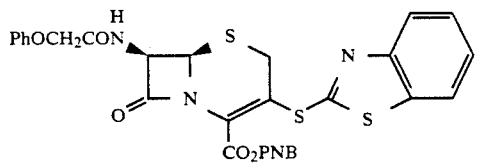

A solution of 4-nitrobenzyl 2-[(3R,4R)-4-[(benzothiazol-2-yl)dithio]-3-phenoxyacetamido-2-oxo-azetidin-I-yl]-3-trifluoromethanesulfonyloxy-2-butenoate (XXb, 0.1435 g, 0.000183 mole) in dry tetrahydrofuran (3 mL) was treated at 0° C. with triethylamine (0.026 mL, 0.000183 mole). After 1 h at 0° C., complete conversion to allene Id was shown by reverse-phase HPLC or $^1$H-NMR spectroscopy. The solution was cooled to −40° C. and solid dry lithium chloride (0.063 g, 0.0015 mole) was added in one lot. The temperature was allowed to reach −15° C. over the course of 1 h. Work up which included quenching with dilute acid and extracting into ethyl acetate to give a crude product which was purified by silica gel chromatography (flash, 40% ethyl acetate in hexane) to yield the title compound as a pale yellow solid (0.0752 g, 65%).

ANALYTICAL DATA $^1$H-NMR (CDCl$_3$, 360 MHz): δ 8.0 (d, 2H), 7.9 (d, 1H), 7.74 (d, 1H), 7.45–7.1 (m, 7H), 6.98 (t, 1H), 6.85 (d, 2H), 5.95 (dd, 1H), 5.32 (m, 2H), 5.06 (d, 1H), 4.52 (s, 2H), 3.90 (d, J=18 Hz, 1H), 3.54 (d, J=18 Hz, 1H).

MASS (FAB, thioglycerol): 634 (M+), 602, 217, 201, 167.

EXAMPLE 23

Diphenylmethyl 7-phenylacetamido-3-[(benzothiazol-2-yl)thio]-3-cephem-4-carboxylate (IIc)

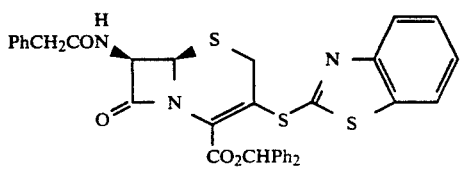

2-Mercaptobenzothiazole (0.59 g, 0.00353 mole) was dissolved in dry dichloromethane (5 mL), and the resulting mixture was treated at 0° C. with sodium hydride (0.141 g of a 1:1 mineral oil dispersion, 0.00294 mole). Evolution of hydrogen was complete in 15 min, and, after cooling to −30° C., the mixture was treated with a solution of diphenylmethyl 7- phenylacetamido-3-trifluoromethanesulfonyloxy-3-cephem-4-carboxylate (IVa, 1.858 g, 0.00294 mole) in dichloromethane (25 mL) over a 1-2 min period. The mixture was stirred 16 h at −15° C. and then 4 h at 0° C. in order to consume all of compound IVa (the reaction was monitered by HPLC). (Reaction at higher temperature induces formation of the Δ$^2$-isomer of compound IIc.) Dilute hydrochloric acid (0.5N, 10 mL) was added to the reaction mixture, followed by extracting the mixture with dichloromethane and drying (sodium sulfate) to yield the title product as a crude product which was recrystallized from dichloromethane/ether at 0° C. overnight.

Yield: 1.37 g (72%) of a tan solid.

ANALYTICAL DATA $^1$H-NMR (CDCl$_3$, 360 MHz): δ 7.95 (d, 1H), 7.78 (d, 1H), 7.5-7.1 (m, 17H), 6.95 (s, 1H), 6.10 (d, J=9 Hz, 1H), 3.83 (d, J=18.0 Hz, 1H), 3.62 (m, 2H), 3.49 (d, J=18.0 Hz, 1H).

EXAMPLE 24

Diphenylmethyl 7-phenylacetamido-3-vinyl-3-cephem-4-carboxylate (IIIa)

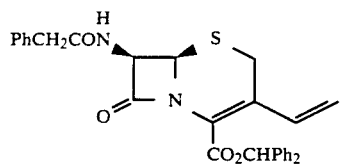

A mixture of diphenylmethyl 7-phenylacetamido-3-[(benzothiazol-2-yl)thio]-3-cephem-4-carboxylate (IIc, 0.0973 g, 0.00015 mole), bis(dibenzylidene acetone)palladium (0.0044 g, 0.00000765 mole), tri(2-furyl)phosphine (0.006 g, 0.000026 mole), zinc chloride (0.042 g, 0.003 mole) and vinyl tributyl stannane (0.055 mL, 0.00018 mole) in dry tetrahydrofuran (3 mL) was heated under argon atmosphere at 65° C. for 18 h. After that period HPLC indicated no further conversion of compound IIc. Water and ethyl acetate was added to the reaction mixture, and the two phases were separated. The organic phase was separated, dried and concentrated. The crude product obtained was dissolved in acetonitrile and the acetonitrile solution was washed three times with equal volumes of pentane. Flash chromatography (5% dichloromethane in ethyl acetate) recovered starting compound IIc (0.041 g, 42%) and afforded product IIIa (0.0133 g, 17%, 29% when corrected for recovered starting material) as a yellow foam. Recrystallization from ethanol gave the analytical sample.

ANALYTICAL DATA $^1$H-NMR (CDCl$_3$, 360 MHz): δ 7.5-7.2 (m, 15H), 7.0-6.8 (m, 3H), 6.05 (br d, J=8.8 Hz, 1H), 5.82 (dd; J=4.4, 8.8 Hz, 1H), 5.38 (d, J=17.7 Hz, 1H), 5.22 (d, J=11.7 Hz, 1H), 4.94 (d, J=4.4 Hz, 1H), 3.75-3.50 (m, 3H), 3.44 (d, J=17.7 Hz, 1H).

Elem. Anal. Calcd for C$_{29}$H$_{26}$N$_2$O$_4$S: C, 70.56; H, 5.13; N, 5.49; S, 6.28.

Found: C, 70.22; H, 5.13; N, 5.21; S, 6.41.

EXAMPLE 25

Diphenylmethyl 7-t-Butoxycarbonyl-3-[(1-methyl-1,2,3,4-tetrazol-5-yl)thio]-3-cephem-4-carboxylate (IId)

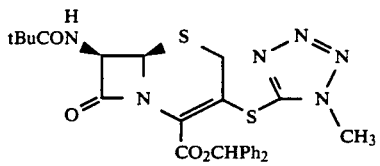

To a solution of diphenylmethyl 7-t-butoxycarbonyl-3-trifluoromethanesulfonyloxy-3-cephem-4-carboxylate (IVb, 3.486 g, 0.00567 mole) in dry tetrahydrofuran (30 mL), 1-methyl-1,2,3,4-tetrazolyl-5-thiol sodium salt hydrate (0.940 g, 0.00725 mole) was added at once, and the solution was stirred at room temperature for 4 h, until HPLC showed a complete consumption of the starting cephem. Normal workup with water and ethyl acetate was followed by flash chromatography (30-40% ethyl acetate in hexane) to yield 2.835 g (86%) of the title product as a white foam.

ANALYTICAL DATA $^1$H-NMR (CDCl$_3$, 360 MHz): δ 7.4-7.20 (m, 15H), 6.97 (s, 1H), 5.66 (m, 1H), 5.28 (br d, 1H), 5.0 (d, J=5 Hz, 1H), 3.80 (d+s, 4H overall), 3.40 (d, J=18 Hz, 1H), 1.42 (s, 9H).

EXAMPLE 26

Diphenylmethyl 7-t-Butoxycarbonyl-3-(Z)-1-propenyl-3-cephem-4-carboxylate (IIIb)

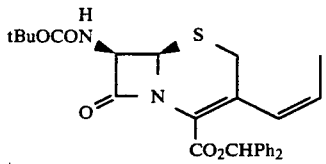

A mixture of diphenylmethyl 7-t-butoxycarbonyl-3-[(1-methyl-1,2,3,4-tetrazol-5-yl)thio]-3-cephem-4-carboxylate (IId, 0.125 g, 0.000215 mole), bis(dibenzylideneacetone)palladium (0.0062 g, 0.00001075 mole), triphenyl phosphine (0.0084 g, 0.000032 mole), zinc chloride (0.0586 g, 0.00043 mole) and Z-1-propenyl-tributyl stannane (0.071 g, 0.000215 mole) in dry tetrahydrofuran (2 mL) was refluxed under argon atmosphere for 20 h. After no further conversion of starting compound IId took place, water and ethyl acetate were added. The organic phase was separated, dried and concentrated. The crude product dissolved in acetonitrile and the acetonitrile solution was washed three times with equal volumes of pentane. Flash chromatography with 20% ethyl acetate in hexane gave the title product (0.022 g, 20%) as a foam. Also recovered was 0.0435g (34.8%) of starting compound IId.

EXAMPLE 27 p-Methoxybenzyl 7-phenylacetamido-3-[(1-methyl1,2,3,4-tetrazol-5-yl)thio]-3-cephem-4-carboxylate (IIe)

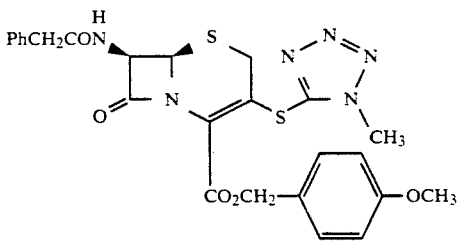

To a solution of p-methoxybenzyl 7-phenylacetamido-3-trifluoromethanesulfonyloxy-3-cephem-4-carboxylate, (1.17 g, 0.0020 mole) in tetrahydrofuran (100 mL), 1-methyl-1,2,3,4-tetrazolyl-5-thiol sodium salt hydrate (0.33 g, 0.0024 mole) was added at once, and the solution was stirred at room temperature for 20 h until HPLC showed complete consumption of the triflate. Workup with water and ethyl acetate followed by crystallization from methanol produced 0.94 g (85%) of the title product.

ANALYTICAL DATA $^1$H-NMR (CDCl$_3$, 360 MHz): δ 7.4–6.8 (m, 9H), 6.1 (br d, 1H), 5.85 (q, 1H), 5.2 (m, 2H), 5.0 (d, 1H), 3.95 (s, 3H), 3.8 (d+s, 4H overall), 3.6 (m, 2H), 3.35 (d, 1H).

EXAMPLE 28 p-Methoxybenzyl 7-phenylacetamido-3-(Z-1-propenyl)-3-cephem-4-carboxylate (IIIc)

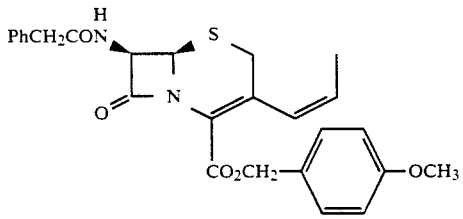

To 0.112 g (0.00050 mole) of palladium (II) acetate in 1.0 mL of dry 1-methyl-2-pyrrolidinone was added 0.331 g (0.0010 mole) of Z-1-propenyl tri-n-butylstannane and the mixture was stirred for 5 min at room temperature under a nitrogen atmosphere. Then 0.276 g (0.00050 mole) of compound IIe and 0.182 g (0.00055 mole) of Z-1-propenyl tri-n-butylstannane were added to the reaction mixture and the resultant mixture stirred at room temperature for 20 h. The HPLC analysis of the reaction mix showed disappearance of compound IIe. The reaction mixture was diluted with ethyl acetate, washed twice with water and finally the organic phase treated with charcoal. The carbon was removed by filtration and the filtrate was concentrated. The residue was purified by silica gel chromatography to yield 0.103 g (43%) of the title compound.

ANALYTICAL DATA $^1$H-NMR (CDCl$_3$, 360 MHz): δ 7.4–6.8 (m, 9H), 6.1 (br d+s, 2H), 5.8 (dd, 1H), 5,68 (m, 1H), 5.15 (s, 2H), 5.0 (d, 1H), 3.8 (s, 3H), 3.65 (m, 2H), 3.3 (q, 2H), 1.5 (dd, 3H).

Elem. Anal. Calcd. for C$_{26}$H$_{26}$N$_2$O$_5$S: C, 65.25; H, 5.48; N, 5.86; S, 6.70.
Found: C, 65.24; H, 5.37; N, 5.74; S, 6.67.

What is claimed is:

1. A process of forming a cephem of formula II

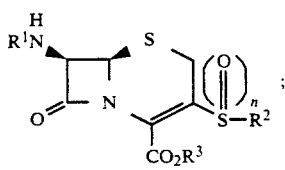

wherein R$^1$ is hydrogen, a conventional amino protecting group or an acyl group; R$^2$ refers to a five-membered aromatic heterocyclic ring containing 1 to 4 nitrogen atoms, and up to 1 sulfur or 1 oxygen atom, said five-membered ring being optionally substituted with up to four C$_{1-6}$ alkyl groups or a benzo group; R$^2$ also may refer to a six-membered aromatic heterocylic ring containing 1 to 4 nitrogen atoms, said six-membered aromatic heterocyclic ring being optionally substituted with up to four C$_{1-6}$ alkyl groups; and said five- or six-membered aromatic heterocylic group being connected to the C-3 sulfur atom of a compound of formula II through an unsubstituted carbon atom in the ring; furthermore, R$^2$ may also refer to phenyl, optionally substituted with one to three halogen, C$_{1-6}$ alkyl, C$_{1-6}$ alkyloxy or C$_{1-6}$ alkylthio; R$^3$ is a conventional carboxy protecting group or —CO$_2$R$^3$ taken together forms a physiologically hydrolyzable ester; and an is 0 or 2;

comprising the step of treating a compound of formula I

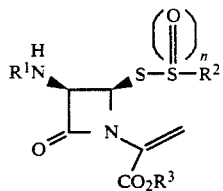

wherein R$^1$, R$^2$, and R$^3$ and n are defined above, with a metal halide selected from the group consisting of zinc, lithium, magnesium, mercuric, boron or aluminum chlorides or bromides.

2. A process as defined in claim 1 in which R$^2$ is benzothiazol-2-yl, benzooxazol-2-yl, 1-methylbenzimidazol-2-yl, 2-pyridyl, oxazol-2-yl, thiazol-2-yl, 1-methyl-1,2,3,4-tetrazol-5-yl, 1-methylimidazol-2-yl, or 4-methylphenyl; R$^1$ is a conventional amino protecting group or an acyl group R$^a$CO—, in which R$^a$ is
hydrogen;
C$_{1-6}$ alkyl, C$_{1-6}$ alkyl substituted by cyano, carboxy, halogen, amino, C$_{1-6}$ alkyloxy, C$_{1-6}$ alkylthio, trifluoromethyl, or trifluoromethylthio;
a phenyl or substituted phenyl group represented by the formula

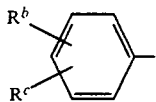

wherein $R^b$ and $R^c$ independently are hydrogen, halogen, hydroxy, $C_{1-6}$ alkyloxy, $C_{1-6}$ alkyl, $C_{1-6}$ alkylthio, amino, mono- or di($C_{1-6}$ alkyl)amino, $C_{1-6}$ alkanoylamino, $C_{1-6}$ alkylsulfonylamino, carboxy, carbamoyl, hydroxymethyl, aminomethyl, or carboxymethyl;

a group presented by the formula

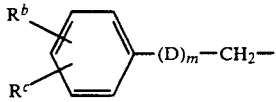

wherein $R^b$ and $R^c$ have the same meanings as defined above, D is oxygen or sulfur, and m is 0 is 1;

a heteroarylmethyl group represented by the formula

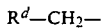

wherein $R^d$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_{1-6}$ alkyl, $C_{1-6}$ alkyloxy, $C_{1-6}$ alkylsulfonylamino;

a substituted methyl group represented by the formula

wherein $R^e$ is cyclohex-1,4-dienyl, or a phenyl group or substituted phenyl group

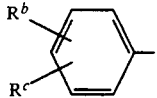

wherein $R^b$ and $R^c$ have the above defined meanings, or $R^3$ is $R^d$ as defined above, and Z is hydroxy, $C_{1-6}$ alkanoyloxy, carboxy, sulfo, or amino;

a keto group or an oximino-substituted group represented by the formulae

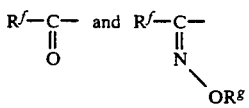

wherein $R^f$ is $R^d$ or $R^e$ as defined above and $R^g$ is hydrogen, $C_{1-6}$ alkyl, cyclic $C_{3-6}$ alkyl or a radical selected from the formulae

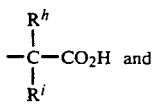

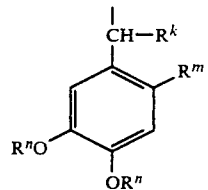

in which $R^h$ and $R^i$ are independently hydrogen, methyl or ethyl, or $R^h$ and $R^i$, taken together with the carbon atom to which they are attached, may be a cycloalkylidene ring containing from 3 to 5 carbon atoms, $R^k$ and $R^m$ are hydrogen, or carboxy, with the proviso that both cannot be the same, and $R^n$ is hydrogen or acetyl; or an alkyldiene group of the formulae

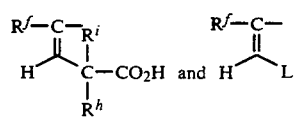

in which L is halogen or $CF_3$, and $R^f$, $R^i$ and $R^h$ are as defined above.

3. A process as defined in claim 1 or 2 in which the metal halide is lithium bromide or lithium chloride.

4. A process as defined in claim 3 in which $R^1$ is phenoxyacetyl, t-butoxycarbonyl or phenylacetyl; $R^2$ is benzothiazol-2-yl, 4-methylphenyl or 1-methyl-1,2,3,4-tetrazol-5-yl; and $R^3$ is diphenylmethyl or 4-nitrobenzyl.

5. A process as defined in claim 4 in which $R^1$ is phenoxyacetyl, $R^2$ is 4-methylphenyl, $R^3$ is diphenylmethyl and n is 2.

6. A process as defined in claim 4 in which $R^1$ is phenoxyacetyl, $R^2$ is benzothiazol-2-yl, $R^3$ is 4-nitrobenzyl and n is 0.

7. A process of forming a cephem of formula III

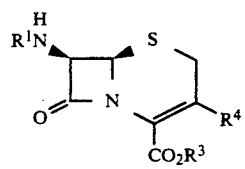

wherein $R^1$ is hydrogen, a conventional amino protecting group or an acyl group; $R^4$ is a group selected from the group consisting of $C_{1-6}$ alkyl, $C_{2-6}$ alkenyl, $C_{2-6}$ alkynyl, cyclic $C_{3-6}$ alkyl and phenyl, optionally substituted with one to three halogen, $C_{1-6}$ alkyl, $C_{1-6}$ alkyloxy or $C_{1-6}$ alkylthio; and $R^3$ is a conventional carboxy protecting group or —$CO_2R^3$ taken together forms a physiologically hydrolyzable ester;

comprising the step of treating a compound of formula II

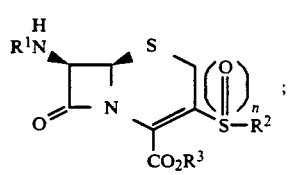

wherein $R^2$ refers to a five-membered aromatic heterocyclic ring containing 1 to 4 nitrogen atoms, and up to 1 sulfur or 1 oxygen atom, said five-membered ring being optionally substituted with up to four $C_{1-6}$ alkyl groups or a benzo group; $R^2$ also may refer to a six-membered aromatic heterocyclic ring containing 1 to 4 nitrogen atoms, said six-membered aromatic heterocylic ring being optionally substituted with up to four $C_{1-6}$ alkyl groups; and said five- or six-membered aromatic heterocyclic group being connected to the C-3 sulfur atom of a compound of formula II through an unsubstituted carbon atom in the ring; furthermore, $R^2$ may also refer to phenyl, optionally substituted with one to three halogen, $C_{1-6}$ alkyl, $C_{1-6}$ alkyloxy or $C_{1-6}$ alkylthio; $R^1$ and $R^3$ are as defined above, and n is 0 or 2; with at least an equimolar amount of $R^4$-tri-$C_{1-6}$ alkylstannane in the presence of about 1–10 mole % of a Pd compound, wherein $R^4$ is as defined above.

8. A process according to claim 7 wherein $R^1$ is a conventional amino protecting group or an acyl group $R^aCO-$, in which $R^a$ is hydrogen;

$C_{1-6}$ alkyl, $C_{1-6}$ alkyl substituted by cyano, carboxy, halogen, amino, $C_{1-6}$ alkyloxy, $C_{1-6}$ alkylthio, trifluoromethyl, or trifluoromethylthio;

a phenyl or substituted phenyl group represented by the formula

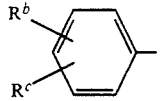

wherein $R^b$ and $R^c$ independently are hydrogen, halogen, hydroxy, $C_{1-6}$ alkyloxy, $C_{1-6}$ alkyl, $C_{1-6}$ alkylthio, amino, mono- or di($C_{1-6}$ alkyl)amino, $C_{1-6}$ alkanoylamino, $C_{1-6}$ alkylsulfonylamino, carboxy, carbamoyl, hydroxymethyl, aminomethyl, or carboxymethyl;

a group presented by the formula

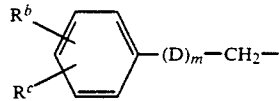

wherein $R^b$ and $R^c$ have the same meanings as defined above, D is oxygen or sulfur, and m is 0 or 1;

a heteroarylmethyl group represented by the formula

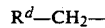

wherein $R^d$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_{1-6}$ alkyl, $C_{1-6}$ alkyloxy, $C_{1-6}$ alkylsulfonylamino;

a substituted methyl group represented by the formula

wherein $R^e$ is cyclohex-1,4-dienyl, or a phenyl group or substituted phenyl group

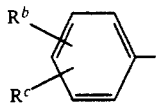

wherein $R^b$ and $R^c$ have the above defined meanings, or $R^e$ is $R^d$ as defined above, and Z is hydroxy, $C_{1-6}$ alkanoyloxy, carboxy, sulfo, or amino;

a keto group or an oximino-substituted group represented by the formulae

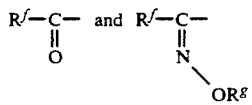

wherein $R^f$ is $R^d$ or $R^e$ as defined above and $R^g$ is hydrogen, $C_{1-6}$ alkyl, cyclic $C_{3-6}$ alkyl or a radical selected from the formulae

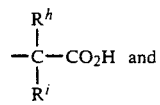

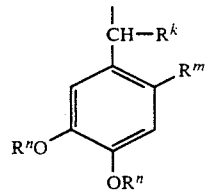

in which $R^h$ and $R^i$ are independently hydrogen, methyl or ethyl, or $R^h$ and $R^i$, taken together with the carbon atom to which they are attached, may be a cycloalkylidene ring containing from 3 to 5 carbon atoms, $R^k$ and $R^m$ are hydrogen or carboxy, with the proviso that both cannot be the same, and $R^n$ is hydrogen or acetyl; and an alkylidene group of the formulae

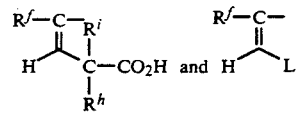

in which L is halogen or $CF_3$, and $R^f$, $R^i$ and $R^h$ are as defined above.

9. A process according to claim 8 wherein the Pd compound is $Pd(dba)_2$ or $Pd(OAc)_2$.

10. A process according to claim 9 wherein the reaction is carried out in the presence of about 3–30 mole % of a phosphine reagent and at least an equimolar amount of a metal halide selected from the group consisting of zinc, lithium, magnesium, mercuric, boron or aluminium chlorides or bromides.

11. A process according to claim 10 wherein the metal halide is zinc chloride.

12. A process according to in any one of claims 7 to 11 wherein n is 0 and $R^2$ is benzothiazol-2-yl, benzooxazol-2-yl, 1-methylbenzimidazol-2-yl, 2-pyridyl, oxazol- 2-yl, thiazol-2-yl, 1-methyl-1,2,3,4-tetrazol-5-yl, or 1-methylimidazol-2-yl.

13. A process according to in claim 12 in which $R^4$-tri-$C_{1-6}$ alkylstannane is selected from the group of $H_2C=CH-SnBu_3$ and $(Z)-CH_3-CH=CH-SnBu_3$.

14. A process according to claim 13 wherein $R^1$ is phenylacetyl or t-butoxycarbonyl, $R^2$ is 1-methyl-1,2,3,4-tetrazol-5-yl or benzothiazol-2-yl, and $R^3$ is diphenylmethyl or p-methoxybenzyl.

15. The process according to claim 14 wherein $R^1$ is phenylacetyl, $R^2$ is benzothiazol-2-yl and $R^3$ is diphenylmethyl.

16. The process according to claim 14 wherein $R^1$ is t-butoxycarbonyl, $R^2$ is 1-methyl-1,2,3,4-tetrazol-5-yl, and $R^3$ is diphenylmethyl.

17. The process according to claim 14 wherein $R^1$ is phenylacetyl, $R^2$ is 1-methyl-1,2,3,4-tetrazol-5-yl, and $R^3$ is p-methoxybenzyl.

* * * * *